United States Patent
Okumura et al.

(10) Patent No.: US 10,709,224 B2
(45) Date of Patent: Jul. 14, 2020

(54) DEVICE CONTROL SYSTEM, WEARABLE DEVICE, INFORMATION PROCESSING DEVICE, FRAGRANCE MATERIAL EJECTION METHOD, AND DEVICE CONTROL METHOD

(71) Applicant: Panasonic Intellectual Property Management Co., Ltd., Osaka (JP)

(72) Inventors: Yasuaki Okumura, Kyoto (JP); Hiroto Yanagawa, Osaka (JP); Yumiko Ohno, Osaka (JP); Yuichi Aoki, Osaka (JP); Mikiya Nakata, Nara (JP); Akira Asai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 206 days.

(21) Appl. No.: 15/612,048

(22) Filed: Jun. 2, 2017

(65) Prior Publication Data

US 2017/0354231 A1    Dec. 14, 2017

(30) Foreign Application Priority Data

Jun. 13, 2016  (JP) ................................. 2016-117241

(51) Int. Cl.
*A61M 21/00* (2006.01)
*A45D 34/02* (2006.01)
(Continued)

(52) U.S. Cl.
CPC ............. *A45D 34/02* (2013.01); *A61L 9/125* (2013.01); *A61M 11/005* (2013.01); (Continued)

(58) Field of Classification Search
None
See application file for complete search history.

(56) References Cited

U.S. PATENT DOCUMENTS

| 10,039,445 B1* | 8/2018 | Torch ...................... A61B 3/112 |
| 2002/0078204 A1* | 6/2002 | Newell .................... G06F 1/163 |
| | | 709/225 |

(Continued)

FOREIGN PATENT DOCUMENTS

| JP | 2012-120206 | 6/2012 |
| JP | 2012-121836 | 6/2012 |
| JP | 2015-046065 | 3/2015 |

OTHER PUBLICATIONS

Extended European Search Report, dated Oct. 12, 2017 from the European Patent Office (EPO), for the related European Patent Application No. 17173444.5.

(Continued)

*Primary Examiner* — Thomas C Lee
*Assistant Examiner* — Gary Collins
(74) *Attorney, Agent, or Firm* — Greenblum & Bernstein, P.L.C.

(57) ABSTRACT

A device control system including a wearable device and a server. The wearable device includes a device that ejects a fragrance material, a biological sensor, and a computer. The computer transmits biological data to the server, receives a first control signal, and causes the device to eject a fragrance material upon receipt of the first control signal. The server includes a computer. The computer receives the biological data, estimates user's emotion from the received biological data, and in a case where it is determined that the user has positive emotion by using a result of the estimation, (i) transmits the first control signal to the wearable device and (ii) transmits, to an aroma device, a second control signal for causing the aroma device to eject a fragrance material at a predetermined timing.

17 Claims, 15 Drawing Sheets

(51) Int. Cl.
  *A61M 11/00* (2006.01)
  *A61L 9/12* (2006.01)
  *B05B 12/02* (2006.01)
  *G06K 9/00* (2006.01)

(52) U.S. Cl.
  CPC ............ *A61M 21/00* (2013.01); *B05B 12/02* (2013.01); *G06K 9/00892* (2013.01); *A61M 2021/0016* (2013.01); *A61M 2021/0077* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/505* (2013.01); *A61M 2205/52* (2013.01); *A61M 2205/8206* (2013.01); *A61M 2230/06* (2013.01); *A61M 2230/10* (2013.01); *A61M 2230/205* (2013.01); *A61M 2230/30* (2013.01); *A61M 2230/42* (2013.01); *A61M 2230/50* (2013.01); *A61M 2230/63* (2013.01); *A61M 2230/65* (2013.01)

(56) References Cited

U.S. PATENT DOCUMENTS

| | | | |
|---|---|---|---|
| 2005/0075532 A1 | 4/2005 | Lee et al. | |
| 2006/0206833 A1* | 9/2006 | Capper | H04M 1/7253 715/773 |
| 2010/0044453 A1 | 2/2010 | Porchia et al. | |
| 2010/0134302 A1* | 6/2010 | Ahn | A61B 5/165 340/576 |
| 2010/0163033 A1 | 7/2010 | Hyde et al. | |
| 2010/0309434 A1* | 12/2010 | Van Schijndel | A61L 9/035 352/85 |
| 2012/0077162 A1* | 3/2012 | Veen | A61B 5/16 434/236 |
| 2012/0078065 A1* | 3/2012 | De Lemos | A61B 3/113 600/301 |
| 2014/0057232 A1* | 2/2014 | Wetmore | G09B 19/00 434/236 |
| 2014/0059066 A1* | 2/2014 | Koloskov | H05K 7/02 707/758 |
| 2014/0060150 A1 | 3/2014 | Shaw et al. | |
| 2014/0334653 A1* | 11/2014 | Luna | G05B 15/02 381/332 |
| 2015/0061825 A1 | 3/2015 | Suzuki et al. | |
| 2015/0086951 A1 | 3/2015 | Bulut et al. | |
| 2015/0126268 A1* | 5/2015 | Keilwert | G07F 17/3227 463/23 |
| 2015/0250420 A1* | 9/2015 | Longinotti-Buitoni et al. | A61B 5/6804 600/301 |
| 2016/0005320 A1* | 1/2016 | deCharms | G09B 5/065 434/236 |
| 2016/0022854 A1 | 1/2016 | Shah | |
| 2016/0055236 A1* | 2/2016 | Frank | G06Q 30/02 707/748 |
| 2016/0232244 A1* | 8/2016 | Liu | G06F 16/9535 |
| 2016/0339300 A1* | 11/2016 | Todasco | H04W 4/80 |
| 2017/0011210 A1* | 1/2017 | Cheong | A61B 5/0022 |
| 2017/0042439 A1* | 2/2017 | Yeow | G16H 10/60 |
| 2017/0076403 A1* | 3/2017 | Edwards | B01F 3/04 |
| 2017/0216519 A1* | 8/2017 | Vouillamoz | G04B 37/127 |
| 2018/0071425 A1* | 3/2018 | Jin | A61L 9/14 |

OTHER PUBLICATIONS

Hiromi Akutsu et al., "Changes of Positive and Negative Affect by a Stress Task", The annual report of the Faculty of Education, University of Iwate, vol. 68, pp. 1-8, Feb. 2009.
Communication pursuant to Article 94(3) EPC, dated Jan. 16, 2019, from the European Patent Office (EPO) for the related European Patent Application No. 17173444.5.

* cited by examiner

DEVICE CONTROL SYSTEM, WEARABLE DEVICE, INFORMATION PROCESSING DEVICE, FRAGRANCE MATERIAL EJECTION METHOD, AND DEVICE CONTROL METHOD

BACKGROUND

1. Technical Field

The present disclosure relates to a device control system, a wearable device, an information processing device, a fragrance material ejection method, and a device control method.

2. Description of the Related Art

Conventionally, a method for selecting scent to be added to a product is disclosed (see Japanese Unexamined Patent Application Publication No. 2012-121836 (hereinafter referred to as Patent Literature 1)). In the method disclosed in Patent Literature 1, scent which a subject prefers is determined by designating a scent category and making the subject answer scent that recalls a past memory from the designated category. That is, Patent Literature 1 discloses recalling a past memory from scent.

However, Patent Literature 1 needs further improvements.

SUMMARY

In one general aspect, the techniques disclosed here feature a device control system including: a wearable device; and an information processing device, the wearable device including: a storage in which a fragrance material containing a predetermined scent component is stored, a device that ejects the fragrance material stored in the storage, a biological sensor that detects biological data of a user, a first communication interface, and a first computer, the first computer transmitting the biological data detected by the biological sensor by using the first communication interface, receiving a first control signal for causing the wearable device to eject the fragrance material by using the first communication interface, and causing the device to eject the fragrance material upon receipt of the first control signal, the information processing device including a second communication interface, and a second computer, the second computer receiving the biological data detected by the wearable device by using the second communication interface, estimating user's emotion by arithmetic processing of the received biological data, determining whether or not the user has positive emotion by using a result of the estimation, and in a case where it is determined that the user has positive emotion, (i) transmitting the first control signal to the wearable device by using the second communication interface and (ii) transmitting, to an environment control device holding the fragrance material, a second control signal for causing the environment control device to eject the fragrance material at a predetermined timing after the transmission of the first control signal by using the second communication interface.

According to the aspect, further improvements can be achieved.

It should be noted that general or specific embodiments may be implemented as a system, a method, an integrated circuit, a computer program, a computer-readable storage medium such as a CD-ROM, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
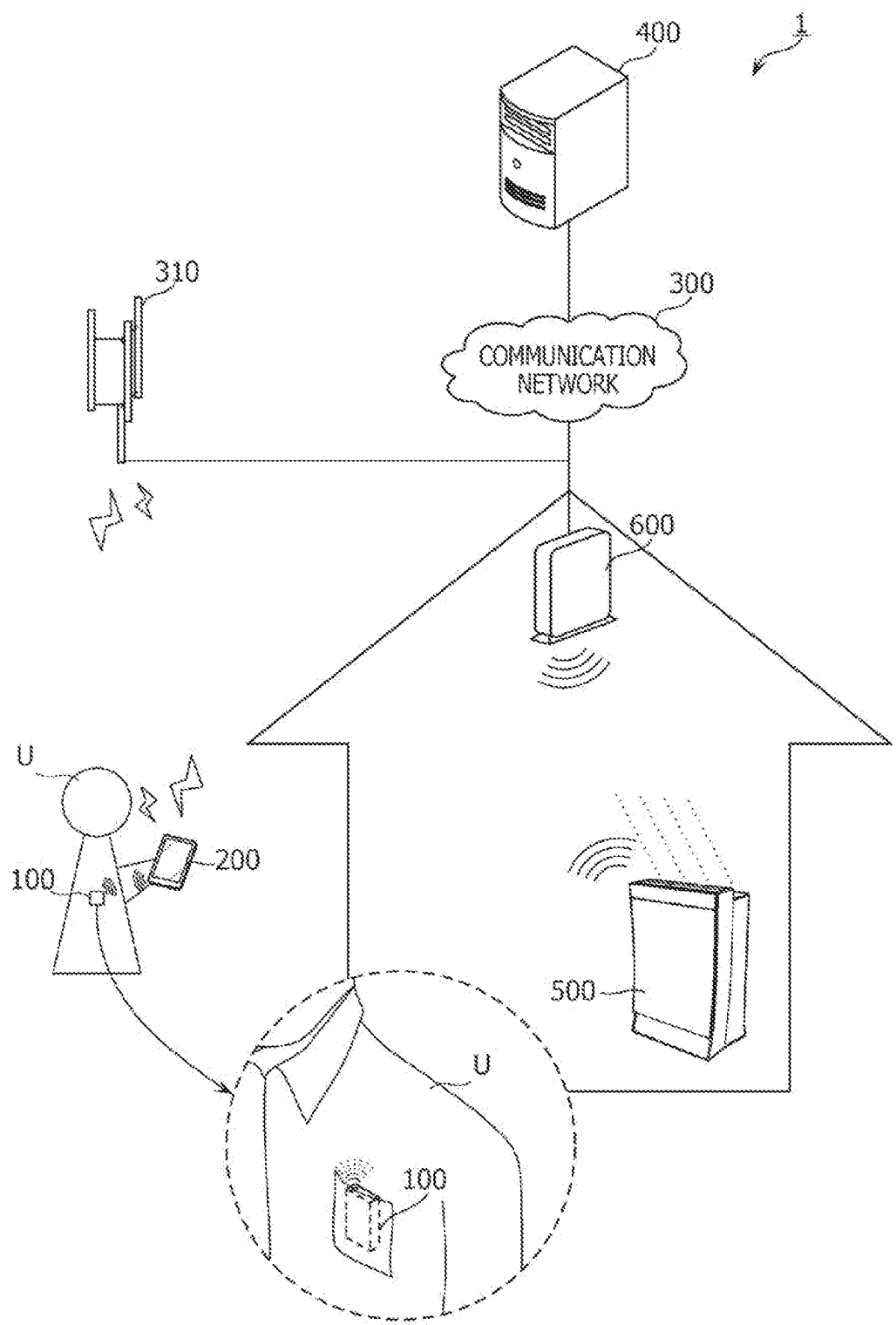
FIG. 1 is a schematic view of a device control system according to an embodiment.

Underlying Knowledge Forming Basis of the Present Disclosure

The inventor of the present invention found that the following problems arise in the selecting method described in BACKGROUND.

It is known that humans feel more happiness and less stress if they recall, for example, three experiences involving positive emotion. However, even if one tries to recall experiences involving positive emotion, it is not easy to recall such experiences involving positive emotion unless the degree of positive emotion is stronger than a predetermined degree. Furthermore, a user subjectively determines whether or not an experience involves positive emotion. It is therefore hard for the user to objectively recall an experience involving positive emotion.

In view of this, the inventor of the present invention considered the following improvements in order to easily make a user recall an experience involving positive emotion.

A device control system according to an aspect of the present disclosure is a device control system including: a wearable device: and an information processing device, the wearable device including: a storage in which a fragrance material containing a predetermined scent component is stored, a device that ejects the fragrance material stored in the storage, a biological sensor that detects biological data of a user, a first communication interface, and a first computer, the first computer transmitting the biological data detected by the biological sensor by using the first communication interface, receiving a first control signal for causing the wearable device to eject the fragrance material by using the first communication interface, and causing the device to eject the fragrance material upon receipt of the first control signal, the information processing device including a second communication interface, and a second computer, the second computer receiving the biological data detected by the wearable device by using the second communication interface, estimating user's emotion by arithmetic processing of the received biological data, determining whether or not the user has positive emotion by using a result of the estimation, and in a case where it is determined that the user has positive emotion, (i) transmitting the first control signal to the wearable device by using the second communication interface and (ii) transmitting, to an environment control device holding the fragrance material, a second control signal for causing the environment control device to eject the fragrance material at a predetermined timing after the transmission of the first control signal by using the second communication interface.

According to this configuration, it is determined whether or not a user has positive emotion on the basis of biological data of the user detected by the biological sensor, and a fragrance material is ejected from the wearable device at a timing at which it is determined that the user has positive emotion. This makes it possible to easily eject a fragrance material from the wearable device at a timing at which it is objectively determined that the user has positive emotion. It is therefore possible to make the user remember an experience objectively involving positive emotion in association with scent contained in the fragrance material.

Furthermore, it is possible to easily make the user recall an experience involving positive emotion by ejecting the fragrance material from an environment control device to the user at a predetermined timing. This makes it possible to improve a user's feeling of happiness and reduce user's stress.

The device control system may be configured such that the second computer further receives positional information indicative of a current position of the user by using the second communication interface and transmits the second control signal to the environment control device at a timing at which it is determined that the current position indicated by the positional information is included in a predetermined positional range as the predetermined timing.

This makes it possible to easily make the user recall an experience involving positive emotion at a timing at which the user is in a relaxing place, for example, at a timing at which the user is at home. It is therefore possible to effectively improve a user's feeling of happiness and reduce user's stress.

The device control system may be configured such that the second computer further counts a current time and transmits the second control signal to the environment control device at a timing at which the counted current time reaches a predetermined time as the predetermined timing.

This makes it possible to easily make the user recall an experience involving positive emotion, for example, at a timing at which the user is relaxed. It is therefore possible to effectively improve a user's feeling of happiness and reduce user's stress.

The device control system may be configured such that the second computer further receives positional information indicative of a current position of the user and schedule information indicative of schedule of the user by using the second communication interface, estimates a situation around the user on basis of a current time, the positional information, and the schedule information, decides at least one of kind and amount of fragrance material to be ejected from the wearable device in accordance with the estimated situation around the user, and transmits, as the first control signal to the wearable device, a control signal for causing the wearable device to eject a fragrance material specified by the at least one of the kind and amount; and the first computer causes the device to eject the fragrance material specified by the at least one of the kind and amount in accordance with the received first control signal.

This makes it possible to eject a fragrance material specified by at least one of kind and amount according to a situation from the wearable device.

The device control system may be configured such that the second computer estimates whether or not the situation around the user is a situation where another person is present within a predetermined distance from the user and makes the amount smaller in a case where it is estimated that another person is present within the predetermined distance from the user than in a case where it is estimated that no other person is present within the predetermined distance from the user.

This makes it possible to reduce the amount of fragrance material ejected from the wearable device in a situation in which another person is present within a predetermined distance from a user, thereby reducing the influence of the fragrance material on the other person.

The device control system may be configured such that the second computer estimates whether or not the situation around the user is a situation where the user is in middle of eating and decides to use scent of forests as the kind in a case where it is estimated that the user is in middle of eating and decides to use any kind of scent as the kind in a case where it is estimated that the user is not in middle of eating.

This makes it possible to eject a fragrance material containing scent of forests that less affects a meal from the wearable device in a situation in which a user is in the middle of eating, thereby reducing the influence of the fragrance material on the meal.

The device control system may be configured such that the storage includes a first storage in which a first fragrance material containing a first scent component is stored as the fragrance material and a second storage in which a second fragrance material containing a second scent component different from the first scent component is stored as the fragrance material; and the device ejects scent different from previously ejected scent by using at least one of the first fragrance material stored in the first storage and the second fragrance material stored in the second storage.

This makes it possible to use different kinds of scent for respective experiences in a case where a user experiences positive emotion plural times, thereby making it possible to easily make the user recall the plurality of experiences. It is therefore possible to effectively improve a users feeling of happiness and reduce user's stress.

A device control system according to another aspect of the present disclosure is a device control system including: a wearable device; and an information processing device, the wearable device including: a storage in which a fragrance material containing a predetermined scent component is stored, a device that ejects the fragrance material stored in the storage, a biological sensor that detects biological data of a user, a first communication interface, and a first computer, the first computer transmitting the biological data detected by the biological sensor by using the first communication interface, receiving a first control signal for causing the wearable device to eject the fragrance material by using the first communication interface, and causing the device to eject the fragrance material upon receipt of the first control signal, the information processing device including a second communication interface, and a second computer, the second computer receiving the biological data detected by the wearable device by using the second communication interface, estimating user's emotion by arithmetic processing of the received biological data, determining whether or not the user has positive emotion by using a result of the estimation, and in a case where it is determined that the user has positive emotion, transmitting the first control signal to the wearable device by using the second communication interface and generating identification information and recording the identification in a memory after the transmission of the first control signal.

According to this configuration, it is determined whether or not a user has positive emotion on the basis of biological data of the user detected by the biological sensor, and a fragrance material is ejected from the wearable device at a timing at which it is determined that the user has positive emotion. This makes it possible to easily eject a fragrance material at a timing at which it is objectively determined that the user has positive emotion. It is therefore possible to make the user remember an experience objectively involving positive emotion in association with scent contained in the fragrance material.

A device control system according to another aspect of the present disclosure is a device control system including: a wearable device; and an information processing device, the wearable device including: a first communication interface, and a first computer, the first computer storing, in a memory, scent information indicative of a scent component of scent that is estimated to have been smelled by a user who is wearing the wearable device when the user has positive emotion and transmitting the scent information by using the first communication interface, the information processing device including a second communication interface, and a second computer, the second computer receiving the scent information by using the second communication interface and transmitting, to an environment control device holding a fragrance material, a control signal for causing the environment control device to eject the fragrance material containing the scent component indicated by the received scent information at a predetermined timing by using the second communication interface.

This makes it possible to easily make a user recall an experience involving positive emotion by ejecting the fragrance material from the environment control device to the user at a predetermined timing. It is therefore possible to improve a users feeling of happiness and reduce user's stress.

A wearable device according to an aspect of the present disclosure is a wearable device including: a storage in which a fragrance material containing a predetermined scent component is stored; a device that ejects the fragrance material stored in the storage; a biological sensor that detects biological data of a user; a communication interface; and a computer, the computer transmitting the biological data detected by the biological sensor by using the communication interface, receiving a control signal for causing the wearable device to eject the fragrance material by using the communication interface, and causing the device to eject the fragrance material upon receipt of the control signal.

According to the configuration, a first control signal that is transmitted at a timing at which it is determined that a user has positive emotion is received by transmitting biological data of the user detected by the biological sensor. This makes it possible to eject a fragrance material at the timing at which the user has positive emotion. It is therefore possible to make the user remember an experience objectively involving positive emotion in association with scent contained in the fragrance material.

An information processing device according to an aspect of the present disclosure is an information processing device that is communicably connected to a wearable device and an environment control device, including: a communication interface; and a computer, the computer receiving biological data of a user wearing the wearable device by using the communication interface, the biological data being detected by the wearable device, estimating user's emotion by arithmetic processing of the received biological data, determining whether or not the user has positive emotion by using a result of the estimation, and in a case where it is determined that the user has positive emotion, (i) transmitting, to the wearable device holding a fragrance material, a first control signal for causing the wearable device to eject the fragrance material by using the communication interface and (ii) transmitting, to the environment control device holding the fragrance material, a second control signal for causing the environment control device to eject the fragrance material at a predetermined timing after the transmission of the first control signal by using the communication interface.

According to this configuration, it is determined whether or not a user has positive emotion on the basis of biological data of the user detected by the biological sensor, and a fragrance material is ejected from the wearable device which the user is wearing at a timing at which it is determined that the user has positive emotion. This makes it possible to easily eject a fragrance material at a timing at which it is objectively determined that the user has positive emotion. It is therefore possible to make the user remember an experience objectively involving positive emotion in association with scent contained in the fragrance material.

Furthermore, it is possible to easily make the user recall an experience involving positive emotion by ejecting the fragrance material from an environment control device to the user at a predetermined timing. This makes it possible to improve a user's feeling of happiness and reduce user's stress.

It should be noted that general or specific embodiments may be implemented as a system, a method, an integrated circuit, a computer program, a computer-readable storage medium such as a CD-ROM, or any selective combination thereof.

A device control system, a wearable device, an information processing device, a fragrance material ejection method, and a device control method according to an aspect of the present disclosure are specifically described with reference to the drawings.

An embodiment described below is a specific example of the present disclosure. Numerical values, shapes, materials, constituent elements, the way in which the constituent elements are disposed and connected, steps, the order of steps, and the like are examples and do not limit the present disclosure. Among constituent elements in the embodiment below, constituent elements that are not described in independent claims indicating highest concepts are described as optional constituent elements.

Embodiment

An embodiment is described below with reference to FIGS. 1 through 13.

1-1. Configuration

FIG. 1 is a schematic view of a device control system according to an embodiment.

Specifically, a wearable device 100, a communication terminal 200, a communication network 300, a base station 310 of a mobile communication system, a server 400, an aroma device 500, and a router 600 are illustrated in FIG. 1. Among these constituent elements, a device control system 1 includes, for example, the wearable device 100, the server 400, and the aroma device 500 that corresponds to an environment control device.

The device control system 1 is a system that controls operation of the wearable device 100 and operation of the aroma device 500.

The wearable device 100 is a device which a user U wears. The communication terminal 200 is a device which the user U owns (carries).

1-1-1. Wearable Device

A hardware configuration of the wearable device 100 is described with reference to FIG. 2.

Figure 2:
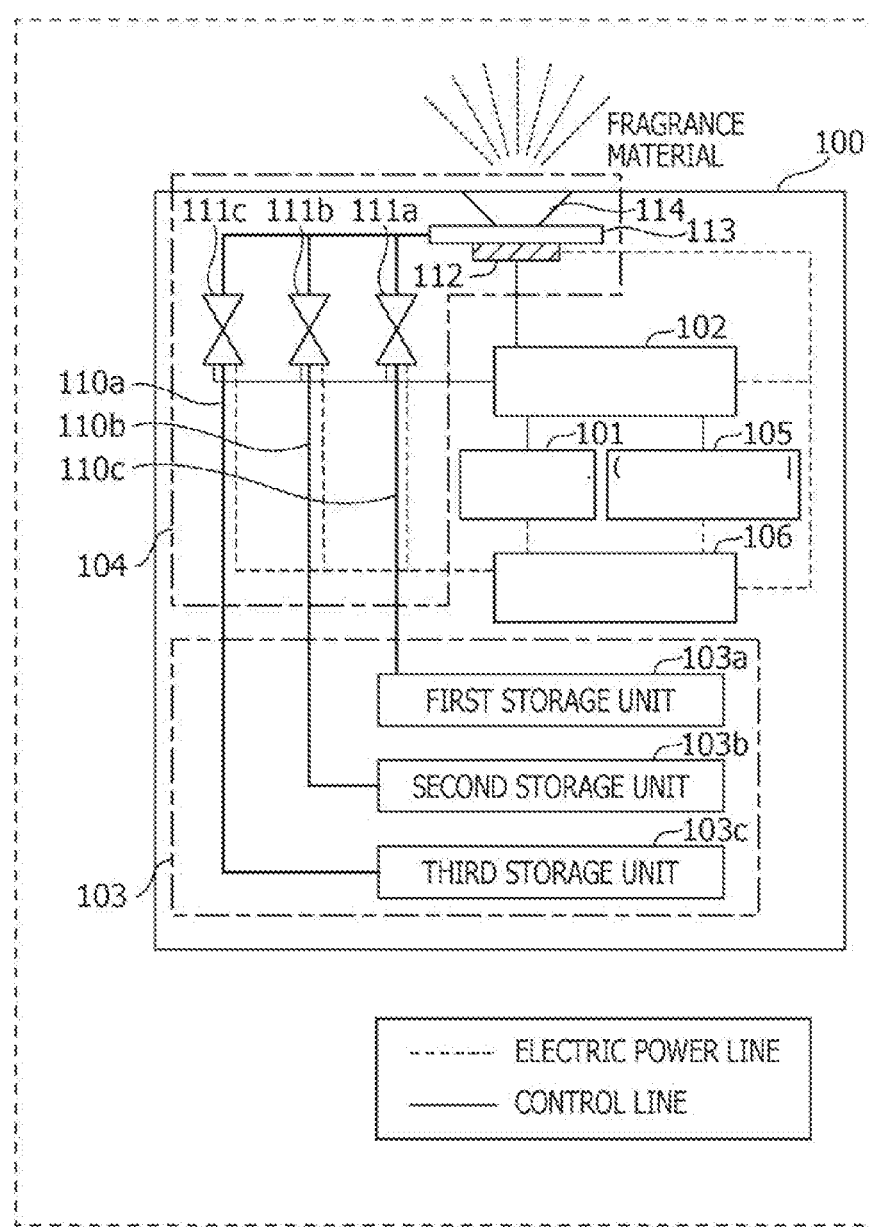
FIG. 2 is a diagram illustrating an example of a hardware configuration of a wearable device according to the embodiment.

FIG. 2 is a diagram illustrating an example of a hardware configuration of the wearable device according to the embodiment.

As illustrated in FIG. 2, the wearable device 100 includes a biological sensor 101, a computer 102, a storage unit 103, a device 104, a communication interface (IF) 105, and a battery 106. The wearable device 100 is, for example, a clip-like terminal attached onto a chest pocket. The wearable device 100 may be a wristwatch-type terminal, a neck-strap-type terminal, eyeglass-type terminal, a head-worn terminal, or an ear-worn terminal. In FIG. 2, the thin solid lines indicate control lines, and the broken lines indicate electric power lines.

The wearable device 100 need not necessarily include the battery 106. Alternatively, the wearable device 100 may be configured to have a container unit that contains a battery and has a connection terminal for electric connection with the battery. In this case, a corresponding battery need be contained in the container unit in order to bring the wearable device 100 into operation.

The biological sensor 101 detects biological data concerning biological functions of a user. The biological data includes, for example, at least one of a heart rate, a heart rate variation, low frequency/high frequency (LF/HF) of a heart rate variation, an R-R interval, pulse waves, a pulse variation, brain waves, a respiratory rate, a respiratory volume, a blood flow, a blood flow variation, a blood pressure, a blood pressure variation, oxygen saturation (SO2), motion of a body part, motion of body muscle, a face color, motion of face muscle, a body temperature, a skin temperature, skin conductance, skin resistance, skin roughness, skin oiliness, skin gas, an amount of perspiration, and a perspiration rate. The motion of a body part is, for example, the frequency or speed of blinking.

The biological sensor 101 includes, for example, at least one of an electrocardiogram sensor (EKG or ECG), a photo plethysmography sensor, an electroencephalograph (EEG), a spirometer, a respirometer, a camera (a visible light camera or a camera having a specific electromagnetic-wave filter), a time-of-flight (TOF) sensor, a millimeter-wave sensor, a millimeter-wave radar, a pulse oximetry, a thermography, a thermal imaging device, an infrared imaging device, a face muscle motion detector, a skin temperature conductance sensor, a skin resistance sensor, a skin gas sensor, a perspiration amount sensor, a near-infrared spectrometer, and a computer tomography (CT) scanner.

The computer 102 includes a processor that executes a control program and a non-volatile memory storing therein the control program.

The storage unit 103 stores therein a fragrance material containing a predetermined scent component. The storage unit 103 includes a first storage unit 103a in which a first fragrance material is stored, a second storage unit 103b in which a second fragrance material is stored, and a third storage unit 103c in which a third fragrance material is stored. The first fragrance material contains a first scent component. The second fragrance material contains a second scent component different from the first scent component. The second scent component may be a scent component that is not contained in the first fragrance material. The third fragrance material contains a third scent component different from the first scent component and the second scent component. The third scent component may be a scent component that is not contained in the first fragrance material and the second fragrance material.

Specifically, the first storage unit 103a, the second storage unit 103b, and the third storage unit 103c are hermetically-sealed containers in which liquid fragrance materials can be stored. The first storage unit 103a, the second storage unit 103b, and the third storage unit 103c are, for example, made of a resin or a metal.

The device 104 is a device that ejects a fragrance material stored in the storage unit 103. The device 104 has flow passages 110a through 110c, valves 111a through 111c, a vibration element 112, a space 113, and a nozzle 114.

The flow passages 110a through 110c are connected to the first storage unit 103a, the second storage unit 103b, and the third storage unit 103c, respectively. The first fragrance material, the second fragrance material, and the third fragrance material flow the flow passages 110a through 110c, respectively. Each of the flow passages 110a through 110c may be a pipe-like member or may be a hole.

The valves 111a through 111c are provided in the flow passages 110a through 110c, respectively. The valves 111a through 111c are valves that can open and close the corresponding flow passages 110a through 110c, respectively.

The vibration element 112 is an element that vibrates so that a fragrance material flowing into the space 113 is sprayed from the nozzle 114. The vibration element 112 is, for example, a piezoelectric element that generates an ultrasonic wave.

The space 113 is a space that is provided on a downstream side of the flow passages 110a through 110c and in which an incoming fragrance material to be sprayed by vibration of the vibration element 112 is stored. The space 113 is a space in which plural kinds of fragrance materials are mixed in a case where the plural kinds of fragrance materials flow into the space 113.

The nozzle 114 is a nozzle for ejecting a fragrance material atomized by the vibration element 112 into an outer space.

The communication IF 105 is a communication interface for communication with the communication terminal 200.

The communication IF 105 may be, for example, a wireless communication interface compatible with a Bluetooth (Registered Trademark) standard or may be a wireless local area network (LAN) interface that is compatible with the IEEE802.11a,b,g,n standard.

The battery 106 supplies electric energy to the biological sensor 101, the computer 102, the device 104, and the communication IF 105. The battery 106 is, for example, a secondary battery.

Although the storage unit 103 includes the three storage units 103a through 103c, the present embodiment is not limited to this. The storage unit 103 may include only one storage unit, may include two storage units, or may include four or more storage units. In this case, a corresponding number of valves and flow passages are provided.

Although the vibration element 112 is a single element common to the three storage units 103a through 103c, the vibration element 112 may be provided for each of the three storage units 103a through 103c. Similarly, the space 113 may be provided for each of the three storage units 103a through 103c. Similarly, the nozzle 114 may be provided for each of the three storage units 103a through 103c.

1-1-2. Communication Terminal

Next, a hardware configuration of the communication terminal 200 is described with reference to FIG. 3.

Figure 3:
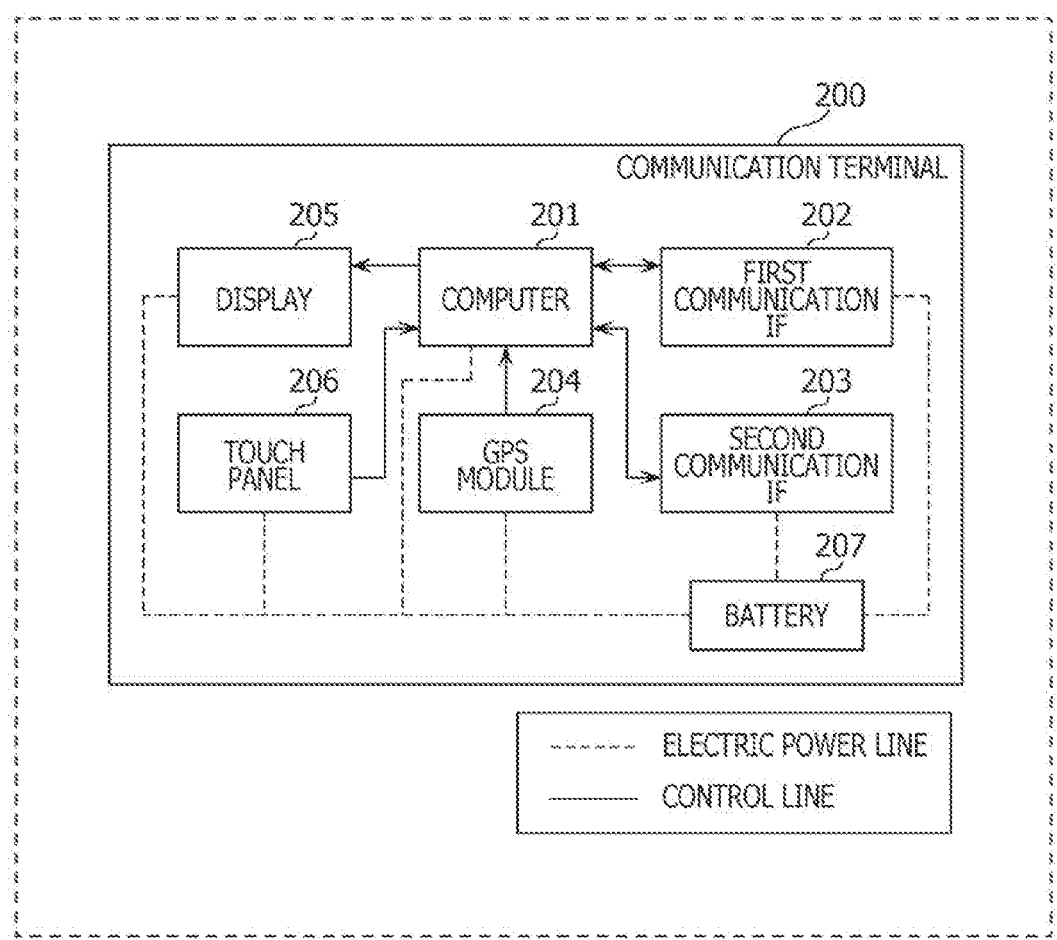
FIG. 3 is a diagram illustrating an example of a hardware configuration of a communication terminal according to the embodiment.

FIG. 3 is a diagram illustrating an example of a hardware configuration of the communication terminal according to the embodiment.

As illustrated in FIG. 3, the communication terminal 200 includes a computer 201, a first communication IF 202, a second communication IF 203, a GPS module 204, a display 205, a touch panel 206, and a battery 207, The communication terminal 200 is a communication terminal which a user of the wearable device 100 owns. The communication terminal 200 is, for example, a mobile terminal such as a smartphone, a tablet terminal, or a mobile router.

The computer 201 includes a processor that executes a control program for causing the communication terminal 200 to operate and a non-volatile memory storing therein the control program.

The first communication IF 202 is a communication interface that communicates with the wearable device 100. The first communication IF 202 can be any communication interface that is compatible with the communication IF 105 of the wearable device 100. That is, the first communication IF 202 may be, for example, a wireless communication interface compatible with a Bluetooth (Registered Trademark) standard or may be a wireless local area network (LAN) interface that is compatible with the IEEE802.11a, b,g,n standard.

The second communication IF 203 is a communication interface that communicates with the server 400 over the communication network 300. That is, the second communication IF 203 may be any communication interface that can be communicably connected to the communication network 300. Specifically, the second communication IF 203 is a communication interface that is communicably connected to the communication network 300 through communication connection with the router 600 or communication connection with the base station 310 of the mobile communication system. The second communication IF 203 may be, for example, a wireless local area network (LAN) interface that is compatible with the IEEE802.11a,b,g,n standard or may be a wireless communication interface that is compatible with a communication standard used in a mobile communication system such as a third-generation mobile communication system (3G), a fourth-generation mobile communication system (4G), or LTE (Registered Trademark).

The first communication IF 202 and the second communication IF 203 may be different communication interfaces so that interference between the wireless communication of the first communication IF 202 and the wireless communication of the second communication IF 203 is prevented.

The GPS module 204 is a module that estimates a position by receiving a signal from a global positioning system (GSP) satellite.

The display 205 is a display device that displays a result of processing in the computer 201. The display 205 is, for example, a liquid crystal display or an organic EL display.

The touch panel 206 is an input device that is disposed on a surface of the display 205 and accepts user's input on a user interface (UI) displayed on the display 205.

The battery 207 supplies electric energy to the computer 201, the first communication IF 202, the second communication IF 203, the GPS module 204, the display 205, and the touch panel 206. The battery 207 is, for example, a secondary battery.

1-1-3. Server

Next, a hardware configuration of the server 400 is described with reference to FIG. 4.

Figure 4:
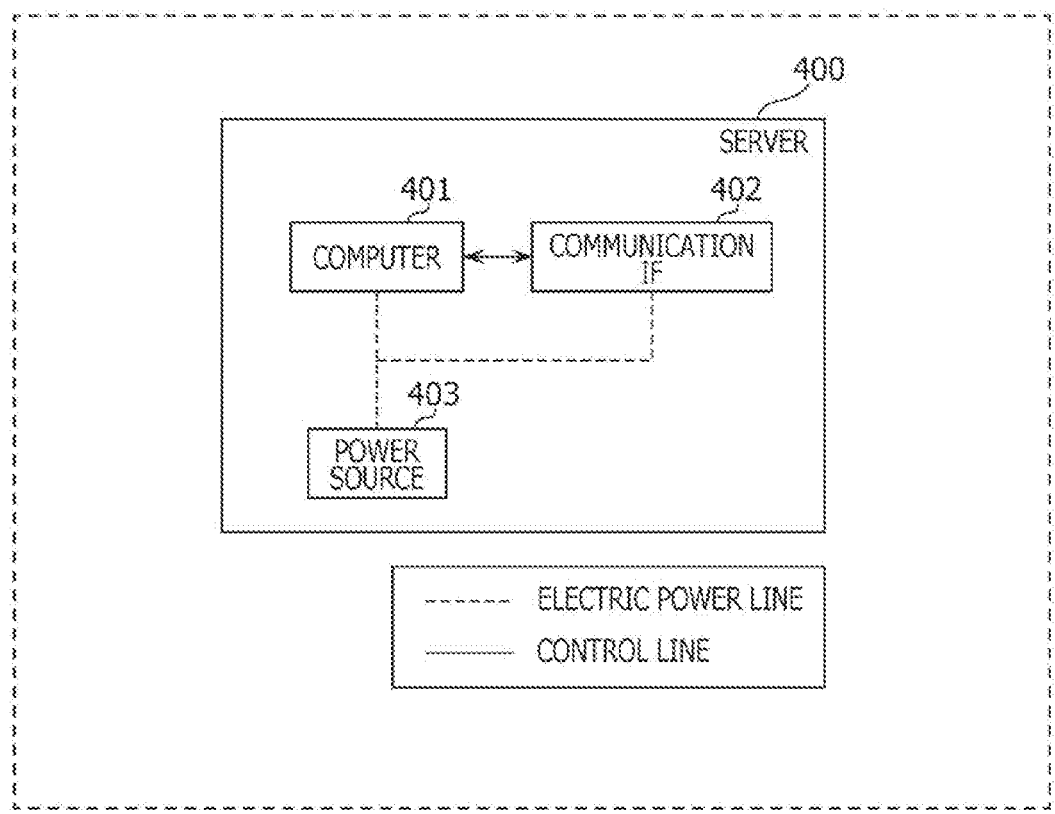
FIG. 4 is a diagram illustrating an example of a hardware configuration of a server according to the embodiment.

FIG. 4 is a diagram illustrating an example of a hardware configuration of the server according to the embodiment.

As illustrated in FIG. 4, the server 400 includes a computer 401, a communication IF 402, and a power source 403. The server 400 is an information processing device for controlling operation of the wearable device 100 and operation of the aroma device 500. The server 400 may be constituted by a plurality of devices.

The computer 401 includes a processor that executes a control program for causing the server 400 to operate and a non-volatile memory storing therein the control program. The control program includes a program for computation concerning emotion estimation that will be described later.

The communication IF 402 is a communication interface that communicates with the communication terminal 200 and the aroma device 500 over the communication network 300. The communication IF 402 is, for example, a wired LAN interface. The communication IF 402 may be a wireless LAN interface. The communication IF 402 is not limited to a LAN interface and can be any communication interface that can establish communication connection with the communication network 300.

The power source 403 supplies electric power to the computer 401 and the communication IF 402 by using electric power supplied from an external power source such as an electric power system. The power source 403 is, for example, an AC/DC converter, a DC/AC inverter, and a DC/DC converter.

1-1-4. Aroma Device

Next, a hardware configuration of the aroma device 500 is described with reference to FIG. 5.

Figure 5:
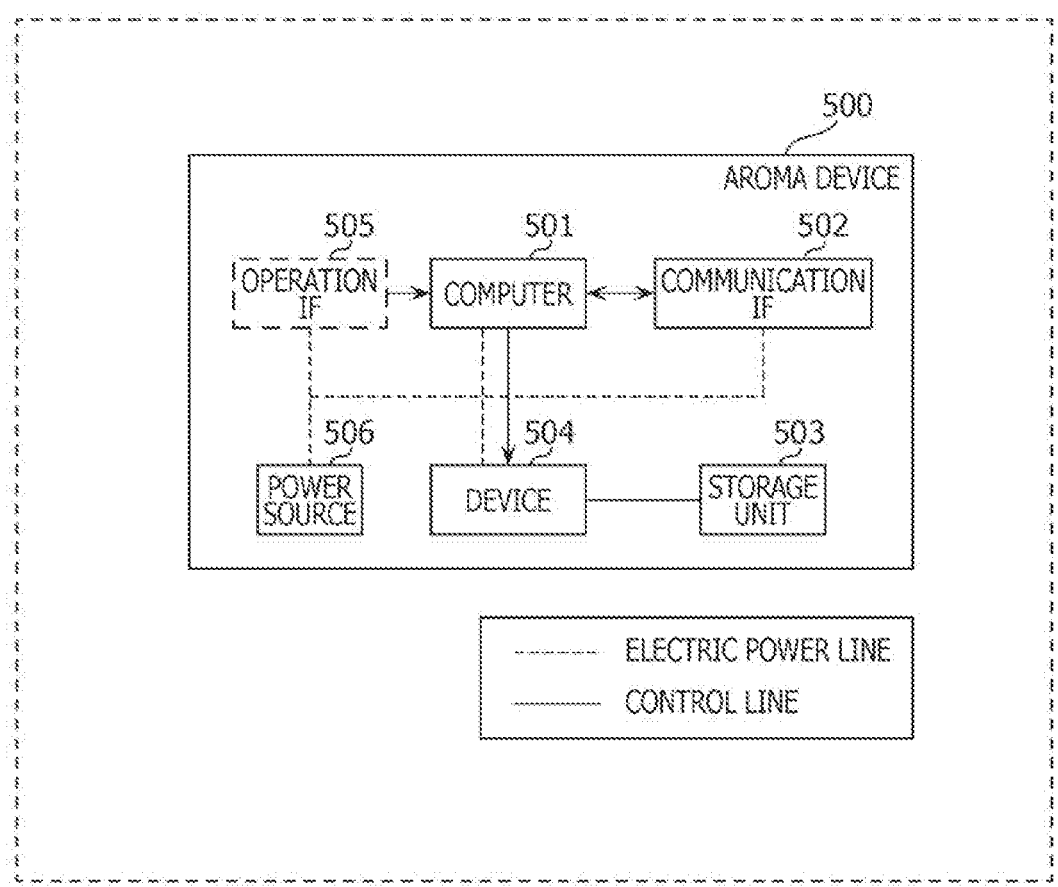
FIG. 5 is a diagram illustrating an example of a hardware configuration of an aroma device according to the embodiment.

FIG. 5 is a diagram illustrating an example of a hardware configuration of the aroma device according to the embodiment.

As illustrated in FIG. 5, the aroma device 500 includes a computer 501, a communication IF 502, a storage unit 503, a device 504, an operation IF 505, and a power source 506. The aroma device 500 is an environment control device that holds a fragrance material containing a predetermined scent component and ejects the held fragrance material. The aroma device 500 is, for example, a stationary device such as an air purifier, an air conditioner, an aroma diffuser, or a humidifier. Alternatively, the aroma device 500 may be incorporated into a lighting device, an electric light bulb, an audio-visual device such as a television set, or any of other household electric appliances such as an electric fan or may be incorporated into furniture or an interior good such as a bed, a table, a sofa, a chair, a tissue case, a wall clock, or a table clock. Alternatively, the aroma device 500 may be incorporated into bed clothing such as a pillow or a mattress or a toy such as a stuffed toy. Alternatively, the aroma device 500 may be a device that can be added later to a household good such as a household electric appliance, furniture, an interior good, bed clothing, or a toy described above.

The computer 501 includes a processor that executes a control program for causing the aroma device 500 to operate and a non-volatile memory storing therein the control program.

The communication IF 502 is a communication interface that communicates with the server 400 over the communication network 300. That is, the communication IF 502 may be any communication interface that can be communicably connected to the communication network 300 and can have a configuration similar to the second communication IF 203.

The storage unit 503 stores therein a fragrance material containing a predetermined scent component. Specifically, the storage unit 503 is functionally similar to the storage unit 103 although a space for storing a fragrance material, a shape, and the like thereof are sometimes different from those of the storage unit 103, and therefore detailed description thereof is omitted.

The device 504 ejects a fragrance material stored in the storage unit 503. Specifically, the device 504 is functionally similar to the device 104 although the size thereof is sometimes different from that of the device 104, and therefore detailed description thereof is omitted.

The operation IF 505 is an operation interface that can accept input for various operations of the aroma device 500. Specifically, the operation IF 505 may be a switch such as a button switch that accepts input or may be a touch panel, The aroma device 500 need not necessarily include the operation IF 505.

The power source 506 supplies electric power to the computer 501, the communication IF 502, the device 504, and the operation IF 505 by using electric power supplied from an external power source such as an electric power system. The power source 506 is, for example, an AC/DC converter, a DC/AC inverter, and a DC/DC converter.

1-1-5. Communication Network

Next, a configuration of the communication network is described with reference to FIG. 1.

The communication network 300 is a communication network over which the wearable device 100, the communication terminal 200, the server 400, the aroma device 500, and the router 600 communicate with one another. The communication network 300 may be a general-purpose network such as the Internet or may be a dedicated network of the device control system 1.

1-1-6. Router

The router 600 can communicate with the communication terminal 200 and the aroma device 500. The router 600 can communicate with the server 400 over the communication network 300 such as the Internet. The router 600 relays communication between the aroma device 500 and the server 400 by communicating with the aroma device 500 and communicating with the server 400 over the communication network 300. For example, the router 600 performs wireless communication with the aroma device 500 and performs wired communication with the server 400.

Furthermore, the router 600 can communicate with the communication terminal 200. The router 600 performs, for example, wireless communication with the communication terminal 200.

1-2. Functional Elements of Device Control System

Next, functional elements of the device control system 1 are described with reference to FIG. 6.

Figure 6:
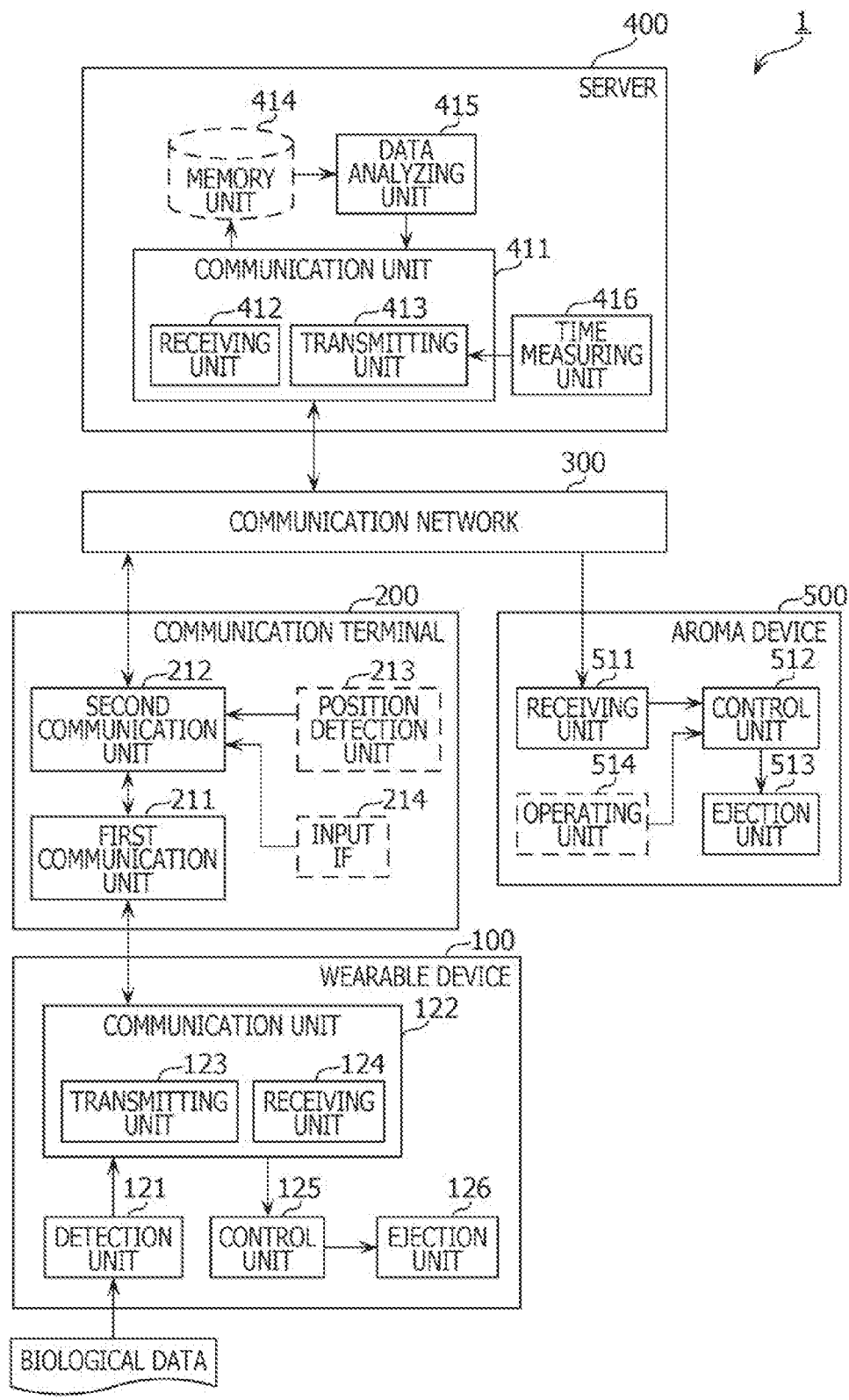
FIG. 6 is a block diagram illustrating an example of functional elements of the device control system.

FIG. 6 is a block diagram illustrating an example of the functional elements of the device control system.

First, functional elements of the wearable device 100 are described.

The wearable device 100 includes, as functional elements, a detection unit 121, a communication unit 122, a control unit 125, and an ejection unit 126.

The detection unit 121 detects biological data of a user. The detection unit 121 is, for example, realized by the biological sensor 101. The detection unit 121 detects biological data of a user, for example, at predetermined time intervals.

The communication unit 122 includes a transmitting unit 123 and a receiving unit 124.

The transmitting unit 123 transmits biological data detected by the detection unit 121 to the server 400. The transmitting unit 123 may transmit biological data to the server 400 every time the biological data is detected by the detection unit 121.

The transmitting unit 123 is, for example, realized by the computer 102 and the communication IF 105. That is, the transmitting unit 123 is a functional element of the computer 102 that transmits biological data to the server 400 connected to the communication network 300 through the communication terminal 200 by using the communication IF 105.

The receiving unit 124 receives, from the server 400, a first control signal for causing the wearable device 100 to eject a fragrance material. The receiving unit 124 is, for example, realized by the computer 102 and the communication IF 105. That is, the receiving unit 124 is a functional element of the computer 102 that receives a first control signal from the server 400 connected to the communication network 300 through the communication terminal 200 by using the communication IF 105.

Upon receipt of the first control signal by the receiving unit 124, the control unit 125 causes the ejection unit 126 to eject a fragrance material. The first control signal may include fragrance material information indicative of the kind of fragrance material, the amount of fragrance material, and the like, and the control unit 125 causes the device 104 to eject a fragrance material of a kind and an amount specified by the fragrance material information included in the first control signal. The control unit 125 is, for example, realized by the computer 102.

The ejection unit 126 ejects a fragrance material upon receipt of a command from the control unit 125. The ejection unit 126 is, for example, realized by the storage unit 103 and the device 104.

Next, functional elements of the communication terminal 200 are described.

The communication terminal 200 includes, as functional elements, a first communication unit 211 and a second communication unit 212. The communication terminal 200 may further include a position detection unit 213 and an input IF 214. In the present embodiment, the communication terminal 200 relays communication connection from the wearable device 100 to the server 400 over the communication network 300. Specifically, the communication terminal 200 receives biological data from the wearable device 100 and transmits the received biological data to the server 400 over the communication network 300. The communication terminal 200 receives a first control signal from the server 400 over the communication network 300 and transmits the received first control signal to the wearable device 100.

The first communication unit 211 establishes communication connection with the communication unit 122 of the wearable device 100 and communicates with the wearable device 100. Furthermore, the first communication unit 211 communicates with the second communication unit 212. The first communication unit 211 receives information (e.g., biological data) from the wearable device 100 and transmits the received information to the second communication unit 212. Furthermore, the first communication unit 211 receives information (e.g., first control signal) from the second communication unit 212 and transmits the received information to the wearable device 100. The first communication unit 211 is, for example, realized by the computer 201, the first communication IF 202, and the like.

The second communication unit 212 communicates with the first communication unit 211. Furthermore, the second communication unit 212 establishes communication connection with the server 400 over the communication network 300 and communicates with the server 400. The second communication unit 212 receives information (e.g., biological data) from the first communication unit 211 and transmits the received information to the server 400. Furthermore, the second communication unit 212 receives information (e.g., first control signal) from the server 400 and transmits the received information to the first communication unit 211. The second communication unit 212 is, for example, realized by the computer 201, the second communication IF 203, and the like.

The position detection unit 213 detects, as positional information, a current position of a user carrying the communication terminal 200. The position detection unit 213 is, for example, realized by the computer 201, the GPS module 204, and the like. Note that the current position of the user is not limited to a position detected by the GPS module 204 and may be, for example, a position estimated by using a radio wave intensity of Wi-Fi (Registered Trademark) or a radio wave intensity of the base station 310 of a mobile telecommunication network.

The input IF 214 is an interface that accepts user's input. The input IF 214 accepts user's input on a predetermined application. For example, the input IF 214 acquires schedule information indicative of user's schedule by accepting input on a schedule management application. The input IF 214 is, for example, realized by the computer 201, the display 205, the touch panel 206, and the like.

The second communication unit 212 may transmit other kinds of information such as positional information detected by the position detection unit 213 or schedule information input by using the input IF 214.

Figure 7:
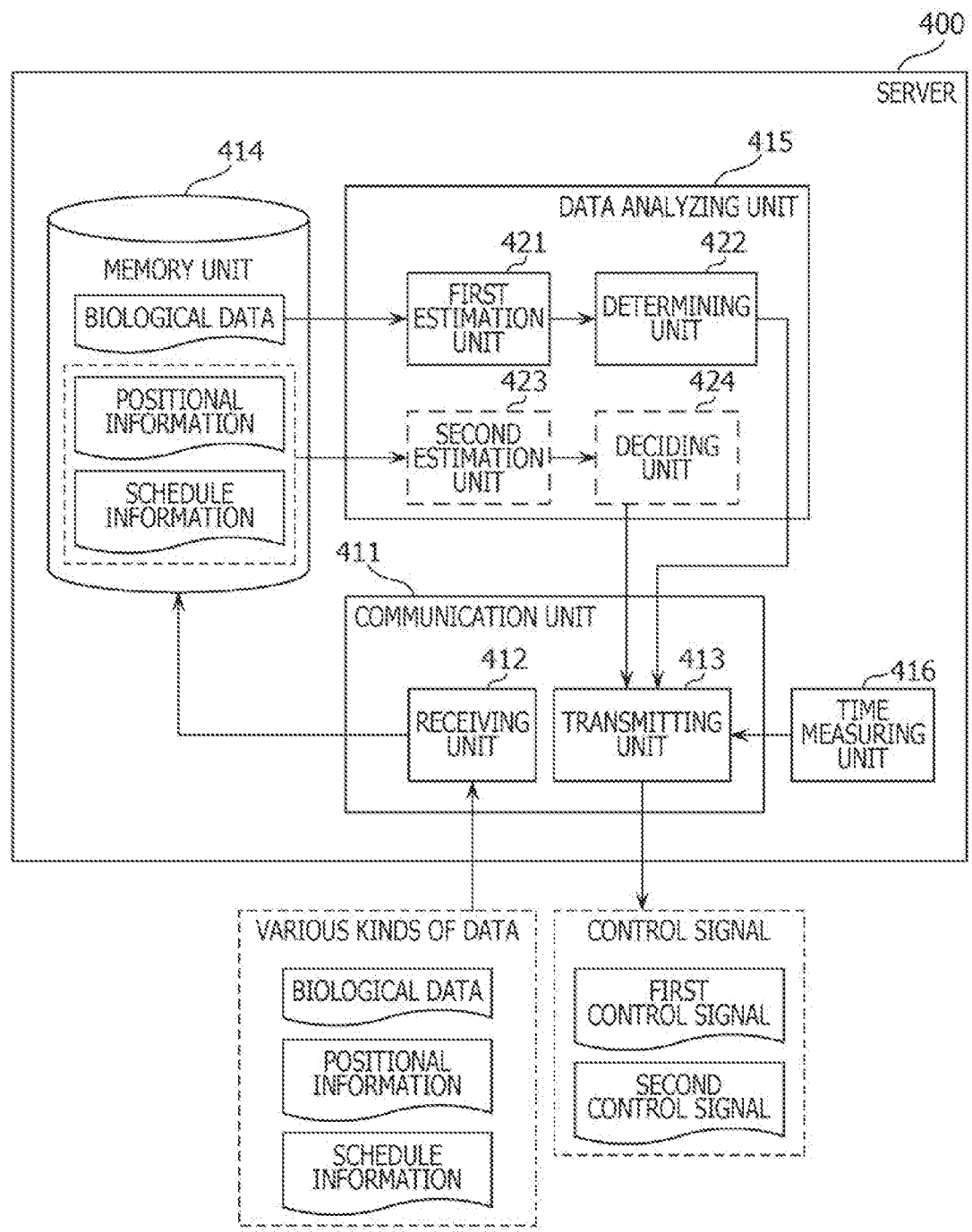
FIG. 7 is a block diagram illustrating an example of functional elements of the server.

Next, functional elements of the server 400 are described. FIG. 7 is a block diagram illustrating an example of functional elements of the server. The functional elements of the server 400 are described with reference to FIGS. 6 and 7.

The server 400 includes, as functional elements, a communication unit 411 and a data analyzing unit 415. The server 400 may further include, as functional elements, a memory unit 414 and a time measuring unit 416. The memory unit 414 may be communicably connected to an outside of the server 400.

The communication unit 411 includes a receiving unit 412 and a transmitting unit 413.

The receiving unit 412 receives biological data from the wearable device 100 over the communication network 300. The receiving unit 412 may receive other kinds of information such as positional information and schedule information from the wearable device 100 over the communication network 300. The receiving unit 412 is, for example, realized by the computer 401 and the communication IF 402. That is, the receiving unit 412 is a functional element of the computer 401 that receives biological data from the wearable device 100 by using the communication IF 402.

The transmitting unit 413 transmits a first control signal and a second control signal generated by the data analyzing unit 415 to the communication terminal 200 and the aroma device 500 over the communication network 300, respectively. The second control signal is a control signal that causes the aroma device 500 to eject a fragrance material at a predetermined timing after transmission of the first control signal. The transmitting unit 413 is, for example, realized by the computer 401 and the communication IF 402. That is, the transmitting unit 413 is a functional element of the computer 401 that transmits the first control signal and the second control signal to the wearable device 100 and the aroma device 500 by using the communication IF 402, respectively, The memory unit 414 stores therein biological data received by the receiving unit 412. The memory unit 414 may further store therein positional information and schedule information of a user received by the receiving unit 412. The memory unit 414 may further store therein user information of the user. That is, in a case where information on a plurality of users are managed, the memory unit 414 may store therein information corresponding to each user such as biological data, positional information, and schedule information in association with user identification information for identifying the user such as a user ID. The memory unit 414 may generate, after transmission of a first control signal from the transmitting unit 413, signal identification information for identifying the transmitted first control signal and store therein the signal identification information in association with user identification information. The memory unit 414 is, for example, realized by a storage such as hard disc drive (HDD) or a solid state drive (SSD) included in the computer 401.

The data analyzing unit 415 generates a first control signal and a second control signal by using biological data, positional information, schedule information, and the like stored in the memory unit 414. A detailed configuration of the data analyzing unit 415 will be described later.

The time measuring unit 416 counts a current time. The time measuring unit 416 is, for example, realized by a timer (not illustrated) provided in the computer 401.

The detailed configuration of the data analyzing unit 415 is described below with reference to FIG. 7.

As illustrated in FIG. 7, the data analyzing unit 415 includes a first estimation unit 421 and a determining unit 422. The data analyzing unit 415 may further include a second estimation unit 423 and a deciding unit 424.

The first estimation unit 421 estimates user's emotion by arithmetic processing of biological data stored in the memory unit 414. The first estimation unit 421 is, for example, realized by the computer 401 and the like.

The determining unit 422 determines whether or not a user has positive emotion by using a result of estimation by the first estimation unit 421. According to "Changes of positive and negative affect by a stress task" Hiromi AKUTSU, Yumi ODASHIMA, Satomi MIYA, The annual report of the Faculty of Education, University of Iwate, Vol. 68 (February 2009) 1-8 (hereinafter referred to as Non Patent Literature 1), "positive emotion" is "an emotional state characterized by happiness, a feeling of happiness, positive valence, and high activation (a sense of wakefulness)" and is specifically "happiness, joy, satisfaction, interest, love, etc.". The determining unit 422 is, for example, realized by the computer 401 and the like.

The second estimation unit 423 estimates a situation around a user on the basis of a current time and positional information. Specifically, the second estimation unit 423 estimates whether or not the situation around the user is a situation where another person is close to the user. Note that the situation where another person is close to the user is, for example, a situation where the user is using public transportation such as a train or a bus during a rush hour such as from 7 a.m. to 9 a.m. or 6 p.m. to 7 p.m.

The situation where another person is close to the user is not limited to the situation where the user is using public transportation and may be a case where the user is at a time and a place that can be estimated to be crowded. In this case, the second estimation unit 423 can estimate whether or not the user is using public transportation during the rush hour or whether or not the user is at crowded time and place on the basis of a current time, positional information, and the like. Specifically, the second estimation unit 423 determines that the situation around the user is a situation where another person is close to the user in a case where the current time and the positional information match a combination of a time zone and a predetermined region that are estimated to be crowded. Otherwise, the second estimation unit 423 determines that the situation around the user is a situation where no other person is close to the user.

Furthermore, the second estimation unit 423 estimates whether or not the situation around the user is a situation where the user is in the middle of eating. In this case, the second estimation unit 423 can estimate that the user is in the middle of eating, for example, in a case where the user is at home or at a restaurant during a time zone in which the user is estimated to be eating by using a current time, positional information, and the like. Specifically, the second estimation unit 423 determines that the user is in the middle of eating in a case where the current time and the positional information match a combination of a time zone and a predetermined region where the user is estimated to be in the middle of eating. Otherwise, the second estimation unit 423 determines that the user is not in the middle of eating.

Note that "a combination of a time zone and a predetermined region that are estimated to be crowded" and "a combination of a time zone and a predetermined region where the user is estimated to be in the middle of eating" may be, for example, generated from big data acquired from users of mobile phones such as smartphones or may be, for example, generated in advance on the basis of input of the user, an application developer, or the like. The second estimation unit 423 can more precisely estimate the situation around the user by using schedule information of the user. The second estimation unit 423 can be, for example, realized by the computer 401 and the like.

Furthermore, the second estimation unit 423 estimates whether or not the situation around the user is a situation where a plurality of persons are in a space in which the user is in, As for a specific example of a method for estimating user's emotion from biological data and determining whether or not the emotion is positive emotion, a known method disclosed in Japanese Unexamined Patent Application Publication No. 2012-120206 (hereinafter referred to as Patent Literature 2) or Japanese Unexamined Patent Application Publication No. 2015-46065 (hereinafter referred to as Patent Literature 3) can be, for example, used.

In Patent Literature 2, a user's psychological state is determined on the basis of a heart rate and a heart rate variation of the user. Specifically, detected heart rate and heart rate variation are compared with respective predetermined threshold values, and it is determined that a user's psychological state is "joy" (i.e., positive emotion) in a case where the heart rate is larger than the predetermined threshold value and where the heart rate variation is larger than the predetermined threshold value.

In Patent Literature 3, a degree of comfort and a degree of wakefulness are generated from a user's biological sensor value obtained by a biological sensor, and user's emotion is estimated from an emotion score that is a combination of the generated degree of comfort and degree of wakefulness. For example, it is determined that user's emotion is a "joy state" (e.g., positive emotion) in a case where the degree of comfort and the degree of wakefulness, which range from −5 to 5, are in a range of approximately "2 to 5" and in a range of approximately "0 to 2", respectively.

The deciding unit 424 decides at least one of the kind and amount of fragrance material to be ejected from the wearable device 100 in accordance with the situation around the user estimated by the second estimation unit 423. That is, the deciding unit 424 changes the kind and amount of fragrance material to be ejected from the wearable device 100 in accordance with the situation around the user.

Specifically, the deciding unit 424 decides to make the amount of fragrance material smaller in a case where the second estimation unit 423 estimates that another person is close to the user than in a case where the second estimation unit 423 estimates that no other person is close to the user. In a case where another person is close to the user, the deciding unit 424 may set the amount of fragrance material to a half of that in a case where no other person is close to the user or may set the amount of fragrance material to 0. In a case where the amount of ejected fragrance material is set to 0, the wearable device 100 ejects no fragrance material.

In a case where the second estimation unit 423 estimates that the user is in the middle of eating, the deciding unit 424 decides to use a kind of fragrance material containing a scent component having a scent of forests as the kind of fragrance material ejected from the wearable device 100. Meanwhile, in a case where the second estimation unit 423 estimates that the user is not in the middle of eating, the deciding unit 424 decides to use a kind of fragrance material containing a scent component having any scent as the kind of fragrance material ejected from the wearable device 100.

Next, information transmitted by the transmitting unit 413 and a timing at which the information is transmitted are described.

The transmitting unit 413 transmits a first control signal to the wearable device 100 in a case where the determining unit 422 determines that a user has positive emotion. The transmitting unit 413 transmits, as the first control signal to the wearable device 100, a control signal for causing the wearable device 100 to eject a fragrance material defined by at least one of the kind and amount of fragrance material decided by the deciding unit 424. The transmitting unit 413 may store a first control signal including information indicative of at least one of the kind and amount of fragrance material so that signal identification information for identifying the first control signal and user identification information are associated with each other.

Furthermore, the transmitting unit 413 transmits a second control signal to the aroma device 500. Specifically, the transmitting unit 413 may transmit a second control signal to the aroma device 500 at a timing at which it is determined that a current position indicated by positional information is included in a predetermined positional range (e.g., user's home) as a predetermined timing. Alternatively, the transmitting unit 413 may transmit a second control signal to the aroma device 500 at a timing at which a current time counted by the time measuring unit 416 reaches a predetermined time (e.g., a time at which the user comes home) as a predetermined timing.

As for the predetermined timing at which the transmitting unit 413 transmits a second control signal to the aroma device 500, the predetermined positional range may be, for example, user's home. In this case, the positional information may be GPS positional information detected by the communication terminal 200 or may be information indicating that the communication terminal 200 is communicable with the router 600 at home. The predetermined time may be, for example, a time zone in which the user is at home. That is, whether or not the user is at home may be estimated by using positional information, may be estimated by using time information, or may be estimated by using positional information and time information.

The predetermined timing may be a timing at which the user arrives home from an outside among timings at which the user is at home. This is because the user is assumed to be more relaxed during a time zone in which the user has arrived home from an outside than during a time zone immediately before leaving home. That is, the server 400 may transmit a second control signal to the aroma device 500 at a timing at which the user is estimated to have arrived home.

A room in which the user is estimated to be relaxed is a predetermined room, and the aroma device 500 is placed in the predetermined room.

Next, functional elements of the aroma device 500 are described.

The aroma device 500 includes, as functional elements, a receiving unit 511, a control unit 512, and an ejection unit 513. The aroma device 500 may further include an operating unit 514 as a functional element.

The receiving unit 511 receives a second control signal from the server 400 over the communication network 300. The receiving unit 511 is, for example, realized by the computer 501, the communication IF 502, and the like.

The control unit 512 causes the ejection unit 513 to eject a fragrance material at a timing at which the receiving unit 511 receives the second control signal. Alternatively, the control unit 512 may cause the ejection unit 513 to eject a fragrance material at a timing at which the operating unit 514 accepts user's operation. The control unit 512 is, for example, realized by the computer 501.

The ejection unit 513 ejects a fragrance material upon receipt of a command from the control unit 512. The ejection unit 513 is, for example, realized by the storage unit 503 and the device 504.

The operating unit 514 accepts a user's operation and transmits an operation signal indicative of the accepted operation to the control unit 512. The operating unit 514 is, for example, realized by the computer 501 and the operation IF 505.

1-3. Operation

Next, operation of the device control system 1 is described with reference to FIGS. 8 through 13.

Figure 8:
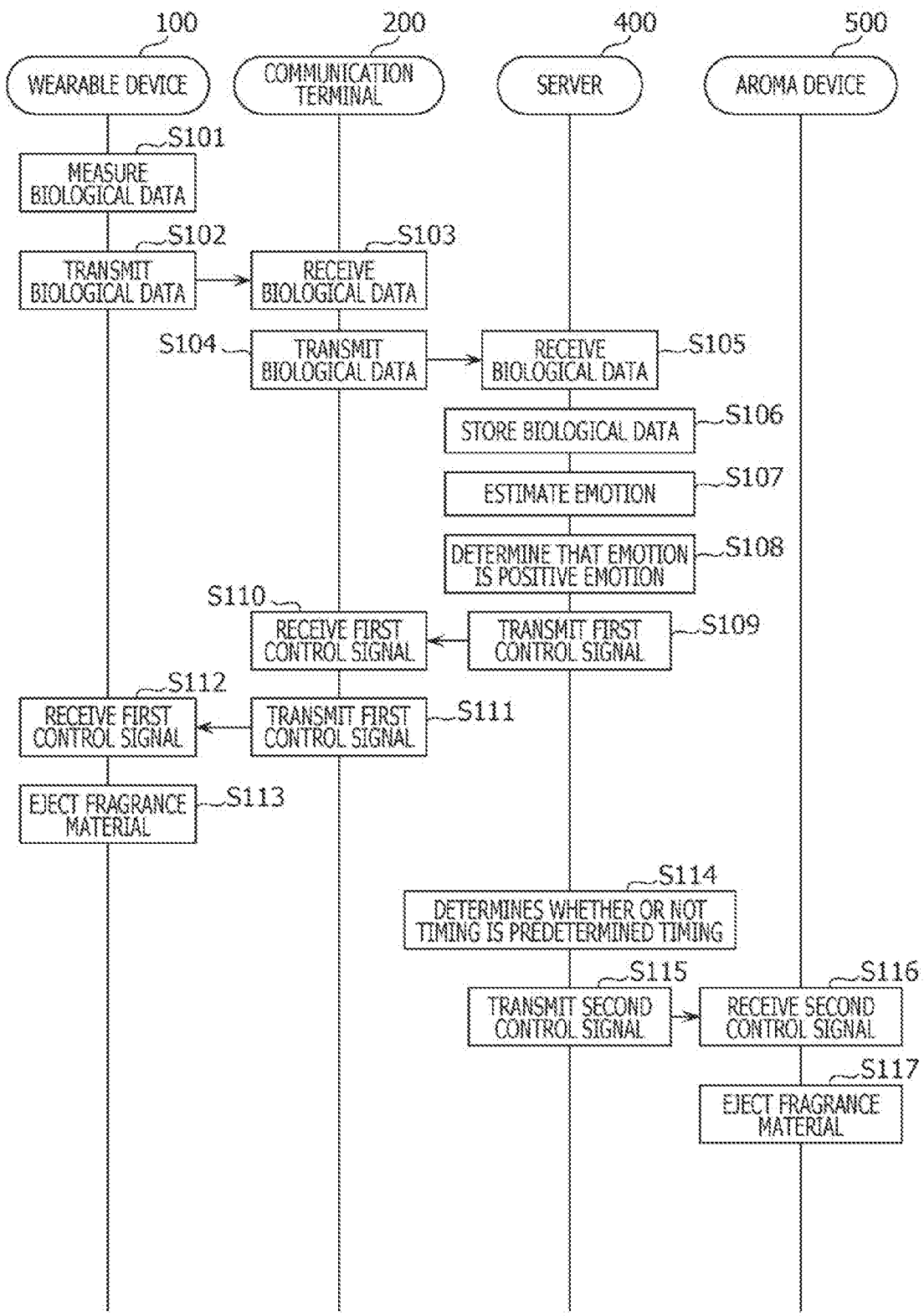
FIG. 8 is a sequence diagram for explaining a device control method in the device control system according to the embodiment.

FIG. 8 is a sequence diagram for explaining a device control method in the device control system according to the embodiment.

First, the wearable device 100 detects biological data of a user wearing the wearable device 100 by using the biological sensor 101 (S101).

Next, the wearable device 100 transmits the biological data detected by the biological sensor 101 to the communication terminal 200 (S102).

The communication terminal 200 receives the biological data from the wearable device 100 (S103) and transmits the received biological data to the server 400 over the communication network 300 (S104).

In the server 400, the receiving unit 412 receives the biological data from the communication terminal 200 (S105), and the memory unit 414 stores therein the received biological data (S106).

In the server 400, the first estimation unit 421 estimates user's emotion by using the biological data stored in the memory unit 414 (S107).

In the server 400, the determining unit 422 determines whether or not the user's emotion is positive emotion by using a result of estimation of the user's emotion by the first estimation unit 421 (S108).

In the server 400, in a case where the determining unit 422 determines that the user's emotion is positive emotion, a first control signal is transmitted to the communication terminal 200 over the communication network 300 (S109).

The communication terminal 200 receives the first control signal from the server 400 (S110) and transmits the received first control signal to the wearable device 100 (S111).

In the wearable device 100, the receiving unit 124 receives the first control signal (S112), and the control unit 125 causes the ejection unit 126 to eject a fragrance material on the basis of the received first control signal (S113).

Then, in the server 400, the transmitting unit 413 determines whether or not a timing is a predetermined timing (S114) and transmits a second control signal to the aroma device 500 over the communication network 300 at the predetermined timing (S115). In the present embodiment, the server 400 transmits the second control signal to the aroma device 500 at a timing at which the user is estimated to have arrived home as the predetermined timing.

In the aroma device 500, the receiving unit 511 receives the second control signal (S116), and the ejection unit 513 ejects a fragrance material on the basis of the received second control signal (S117), Next, a fragrance material ejection method of the wearable device 100 in the device control method is described.

Figure 9:
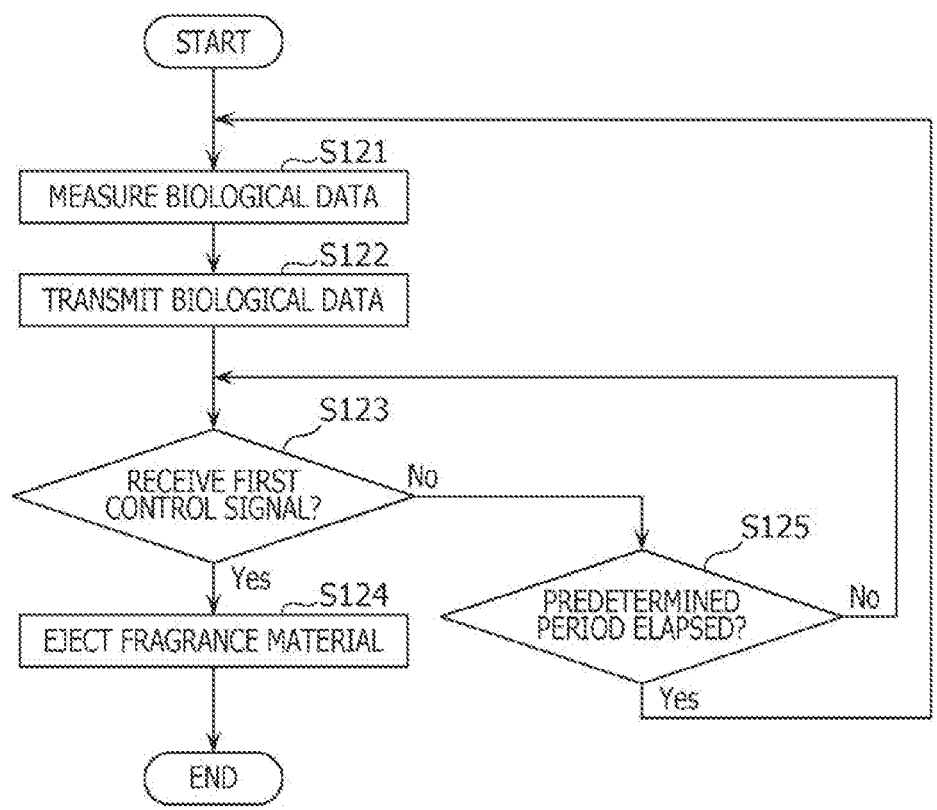
FIG. 9 is a flowchart illustrating a fragrance material ejection method of a wearable device.

FIG. 9 is a flowchart illustrating a fragrance material ejection method of the wearable device.

In the wearable device 100, the biological sensor 101 detects biological data of a user (S121), and the transmitting unit 123 transmits the biological data detected by the biological sensor 101 to the communication terminal 200 (S122).

Then, the wearable device 100 determines whether or not the receiving unit 124 has received a first control signal from the communication terminal 200 (S123).

In a case where the wearable device 100 determines that the receiving unit 124 has received a first control signal from the communication terminal 200 (Yes in S123), the ejection unit 126 ejects a fragrance material (S124). In a case where the wearable device 100 determines that the receiving unit 124 has not received a first control signal from the communication terminal 200 (No in S123), the wearable device 100 determines whether or not a predetermined period has elapsed (S125).

In a case where the wearable device 100 determines that the predetermined period has not elapsed from transmission of the biological data (No in S125), the processing returns to Step S123. That is, the wearable device 100 determines whether or not a first control signal has been received within the predetermined period from transmission of the biological data.

In a case where the wearable device 100 determines that the predetermined period has elapsed from transmission of the biological data (Yes in S125), the processing returns to Step S121. That is, the wearable device 100 determines that the user's emotion is not positive emotion on the basis of the biological data in a case where a first control signal has not been received within the predetermined period from transmission of the biological data, and Step S121 is performed again in order to detect next biological data.

The predetermined period may be, for example, not longer than 1 minute because elapse of a shorter period from transmission of the biological data before ejection of a fragrance material is more preferable.

Next, a method for controlling the wearable device 100 by the server 400 in the device control method is described.

Figure 10:
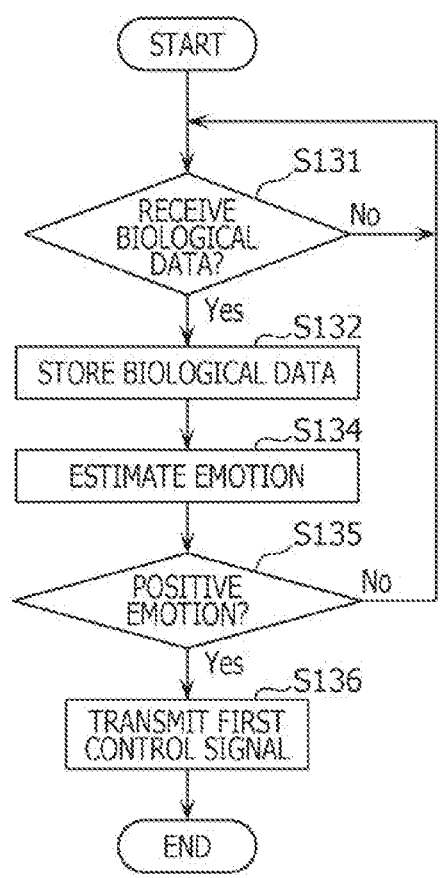
FIG. 10 is a flowchart illustrating a method for controlling the wearable device by the server.

FIG. 10 is a flowchart illustrating a method for controlling the wearable device by the server.

In the server 400, it is determined whether or not the receiving unit 412 has received biological data over the communication network 300 (S131).

In a case where the receiving unit 412 has received biological data (Yes in S131), the memory unit 414 stores the biological data therein (S132). In a case where the receiving unit 412 has not received biological data (No in S131), Step S131 is repeated. That is, the receiving unit 412 waits for reception of biological data.

Next, the first estimation unit 421 of the data analyzing unit 415 estimates user's emotion by using the biological data stored in the memory unit 414 (S134).

Then, the determining unit 422 determines whether or not the user's emotion is positive emotion by using a result of estimation of the user's emotion by the first estimation unit 421 (S135).

In a case where the determining unit 422 determines that the user's emotion is positive emotion (Yes in S135), the transmitting unit 413 transmits a first control signal to the wearable device 100 over the communication network 300 (S136). Meanwhile, in a case where the determining unit 422 determines that the user's emotion is not positive emotion (No in S135), Step S131 is performed again.

In a case where a first control signal is transmitted to the wearable device 100, the server 400 may transmit a first control signal including information indicative of the kind and amount of fragrance material to be ejected from the wearable device 100 in accordance with a situation around the user. In this case, the server 400 acquires positional information and schedule information in order to estimate the situation around the user and then generates the first control signal. Next, a method for generating a first control signal in the server 400 is described.

Figure 11:
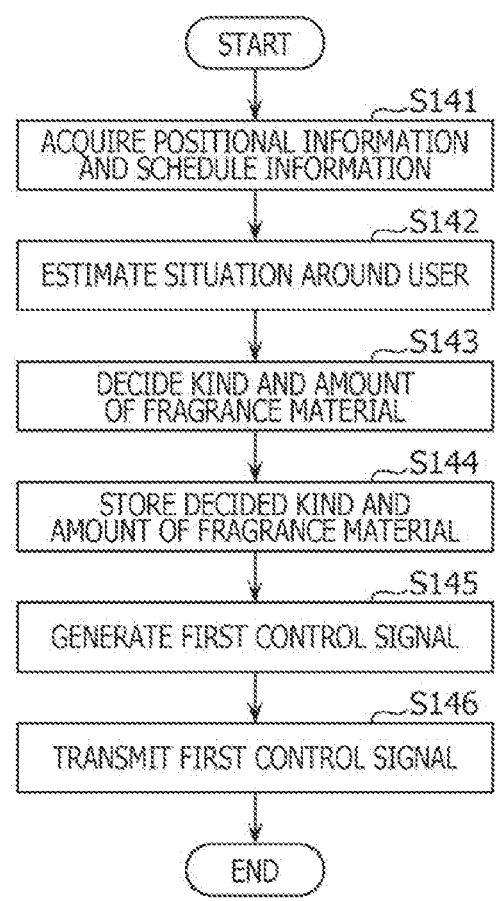
FIG. 11 is a flowchart illustrating a method for generating a first control signal by the server.

FIG. 11 is a flowchart illustrating a method for generating a first control signal by the server.

This generation method may be performed after it is determined in Step S135 of the flow of FIG. 10 that the user's emotion is positive emotion or may be regularly performed without waiting for the determining process in Step S135.

In the server 400, the second estimation unit 423 of the data analyzing unit 415 acquires positional information and schedule information stored in the memory unit 414 (S141).

The data analyzing unit 415 acquires latest ones among the positional information and schedule information stored in the memory unit 414.

The second estimation unit 423 estimates a situation around a user on the basis of a current time, the positional information, and the schedule information (S142). The second estimation unit 423 estimates whether the user is in a situation where another person is close to the user, a situation where the user is in the middle of eating, or a situation other than these situations.

The deciding unit 424 decides the kind and amount of fragrance material to be ejected from the wearable device 100 in accordance with the situation around the user estimated by the second estimation unit 423 (S143). The deciding unit 424 may decide the kind and amount of fragrance material, for example, by referring to a table in which kind and amount are associated with each of the situation where another person is close to the user, the situation where the user is in the middle of eating, and the situation other than these situations. The table is, for example, stored in the memory unit 414. That is, the deciding unit 424 reads out the table from the memory unit 414 and thus decides the kind and amount corresponding to the situation decided by the deciding unit 424.

The memory unit 414 stores therein the kind and amount decided by the deciding unit 424 (S144). In a case where the method for generating a first control signal is performed after the determining process in Step S135, it is unnecessary to perform Step S144 in which the memory unit 414 stores therein the kind and amount decided by the deciding unit 424.

The data analyzing unit 415 generates a first control signal including information indicative of the kind and amount stored in the memory unit 414 (S145).

The transmitting unit 413 transmits the generated first control signal to the wearable device 100 (S146). In a case where the method for generating a first control signal is performed after the determining process in Step S135, the transmitting unit 413 transmits the first control signal to the wearable device 100 promptly after generation of the first control signal. Otherwise, the transmitting unit 413 suspends transmission of the first control signal until it is determined in Step S135 that the user's emotion is positive emotion.

Next, a method for controlling the aroma device 500 by the server 400 in the device control method is described.

Figure 12:
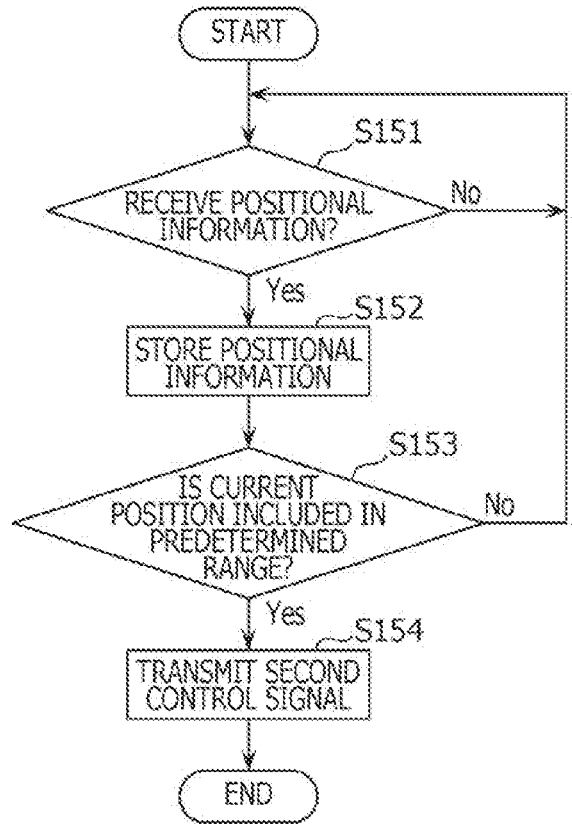
FIG. 12 is a flowchart illustrating an example of a method for controlling the aroma device by the server.

FIG. 12 is a flowchart illustrating an example of a method for controlling the aroma device by the server.

In the server 400, it is determined whether or not the receiving unit 412 has received positional information over the communication network 300 (S151).

In a case where the receiving unit 412 has received positional information (Yes in S151), the memory unit 414 stores the positional information therein (S152). In a case where the receiving unit 412 has not received positional information (No in S151), Step S151 is repeated. That is, the receiving unit 412 waits for reception of positional information.

Next, the data analyzing unit 415 determines whether or not a user's current position is included in a predetermined range (e.g., home) by using the positional information stored in the memory unit 414 (S153).

In a case where the data analyzing unit 415 determines that the user's current position is included in the predetermined range (Yes in S153), the transmitting unit 413 determines that a predetermined timing has arrived and transmits a second control signal to the aroma device 500 over the communication network 300 (S154).

Meanwhile, in a case where the data analyzing unit 415 determines that the user's current position is not included in the predetermined range (No in S153), Step S151 is repeated.

That is, in this flow, the transmitting unit 413 suspends transmission of a second control signal until the predetermined timing arrives.

Figure 13:
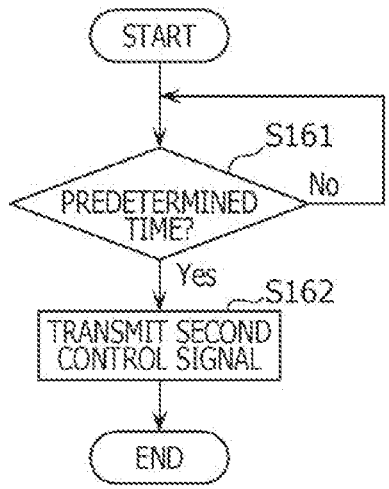
FIG. 13 is a flowchart illustrating another example of a method for controlling the aroma device by the server.

FIG. 13 is a flowchart illustrating another example of the method for controlling the aroma device by the server.

The server 400 determines whether or not a current time is a predetermined time (S161).

In a case where it is determined that the current time is the predetermined time (Yes in S161), the transmitting unit 413 determines that a predetermined timing has arrived and transmits a second control signal to the aroma device 500 over the communication network 300 (S162).

1-4. Effects etc.

Figure 14:
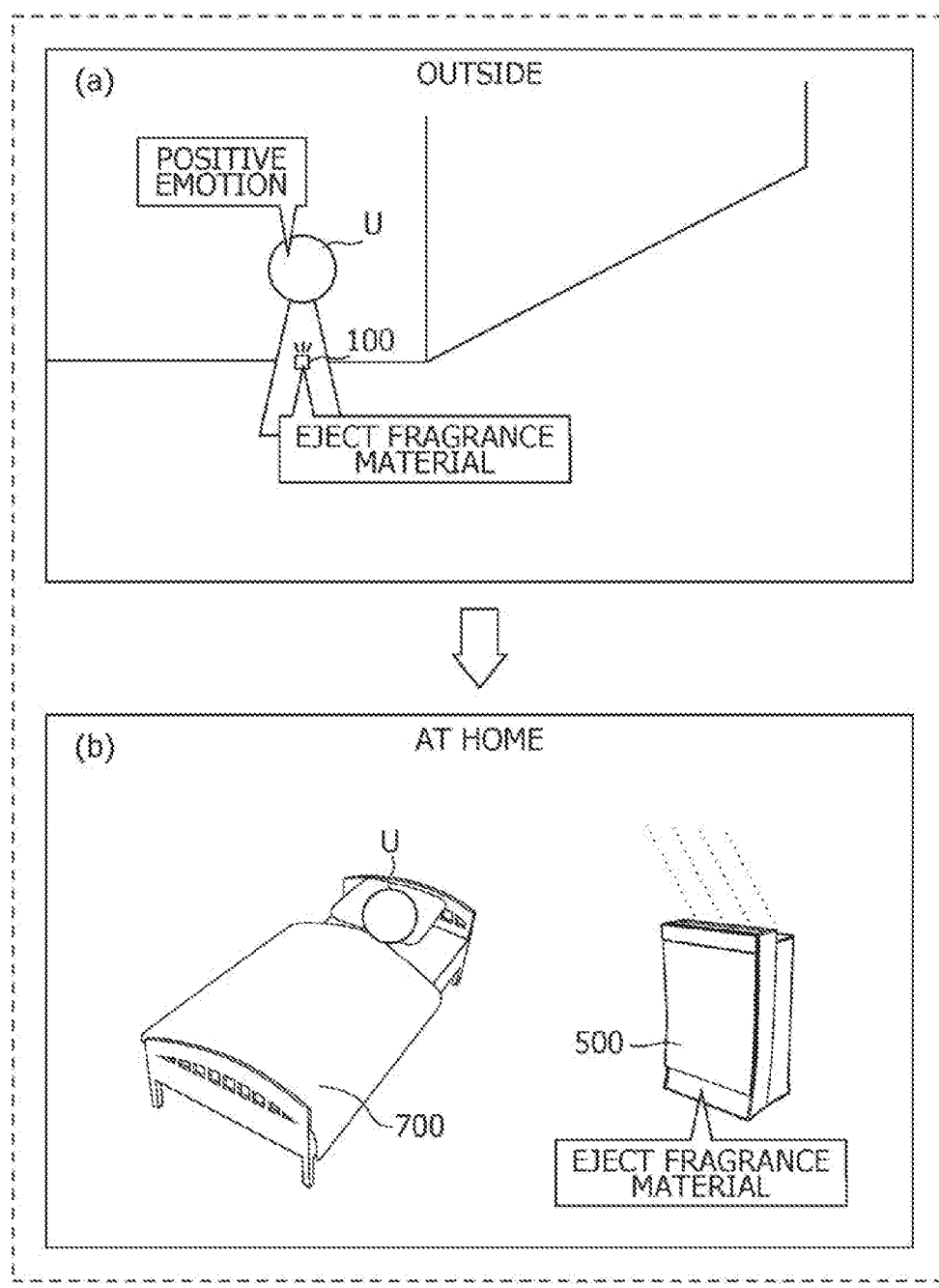
FIG. 14 is a diagram illustrating an example of an aspect of use of the device control system according to the embodiment.

According to the device control system 1 according to the present embodiment, it is determined whether or not a user U has positive emotion on the basis of biological data of the user U detected by the biological sensor 101, and a fragrance material is ejected from the wearable device 100 at a timing at which it is determined that the user U has positive emotion, as illustrated in FIG. 14(*a*). This makes it possible to easily eject a fragrance material from the wearable device 100 at a timing at which it is objectively determined that the user U has positive emotion, for example, when the user U is out. It is therefore possible to make the user U remember an experience objectively involving positive emotion in association with scent included in the fragrance material.

Furthermore, it is possible to easily make the user U recall the experience involving positive emotion by ejecting the fragrance material from the aroma device 500 to the user U at a predetermined timing such as a timing at which the user U is lying on a bed 700 after coming home, as illustrated in FIG. 14(*b*). This makes it possible to improve a feeling of happiness of the user U and to reduce stress of the user U.

The receiving unit 412 of the server 400 receives positional information indicative of a current position of a user, and the transmitting unit 413 transmits a second control signal to the aroma device 500 at a timing at which it is determined that the current position indicated by the positional information is included in a predetermined positional range (e.g., user's home) as a predetermined timing. This makes it possible to easily make the user recall an experience involving positive emotion at a timing at which the user is in a relaxing place, for example, at a timing at which the user is at home. It is therefore possible to effectively improve a user's feeling of happiness and to reduce user's stress.

The transmitting unit 413 of the server 400 transmits a second control signal to the aroma device 500 at a timing at which a current time reaches a predetermined time as a predetermined timing. This makes it possible to easily make a user recall an experience involving positive emotion, for example, at a timing at which the user is relaxed. It is therefore possible to effectively improve a user's feeling of happiness and to reduce user's stress.

In the server 400, the second estimation unit 423 estimates a situation around a user, and the deciding unit 424 decides the kind and amount of fragrance material to be ejected from the wearable device 100 in accordance with a result of estimation by the second estimation unit 423. This makes it possible to eject a fragrance material of kind and amount that correspond to the situation from the wearable device 100. By ejection of the fragrance material from the wearable device 100, the user less frequently experiences discomfort.

Specifically, in the server 400, the amount of fragrance material is made smaller in a situation in which another person is close to the user than in a situation in which no other person is close to the user. With this arrangement, another person close to the user less frequently notices the fragrance material ejected from the wearable device 100.

The server 400 decides to use scent of forests as the kind of fragrance material in a situation in which the user is in the middle of eating. Therefore, even in a case where the user is in the middle of eating, the scent that does not disturb the meal can be used, and the user less frequently experiences discomfort.

1-5. Modifications 1-5-1. Modification 1

Figure 15:
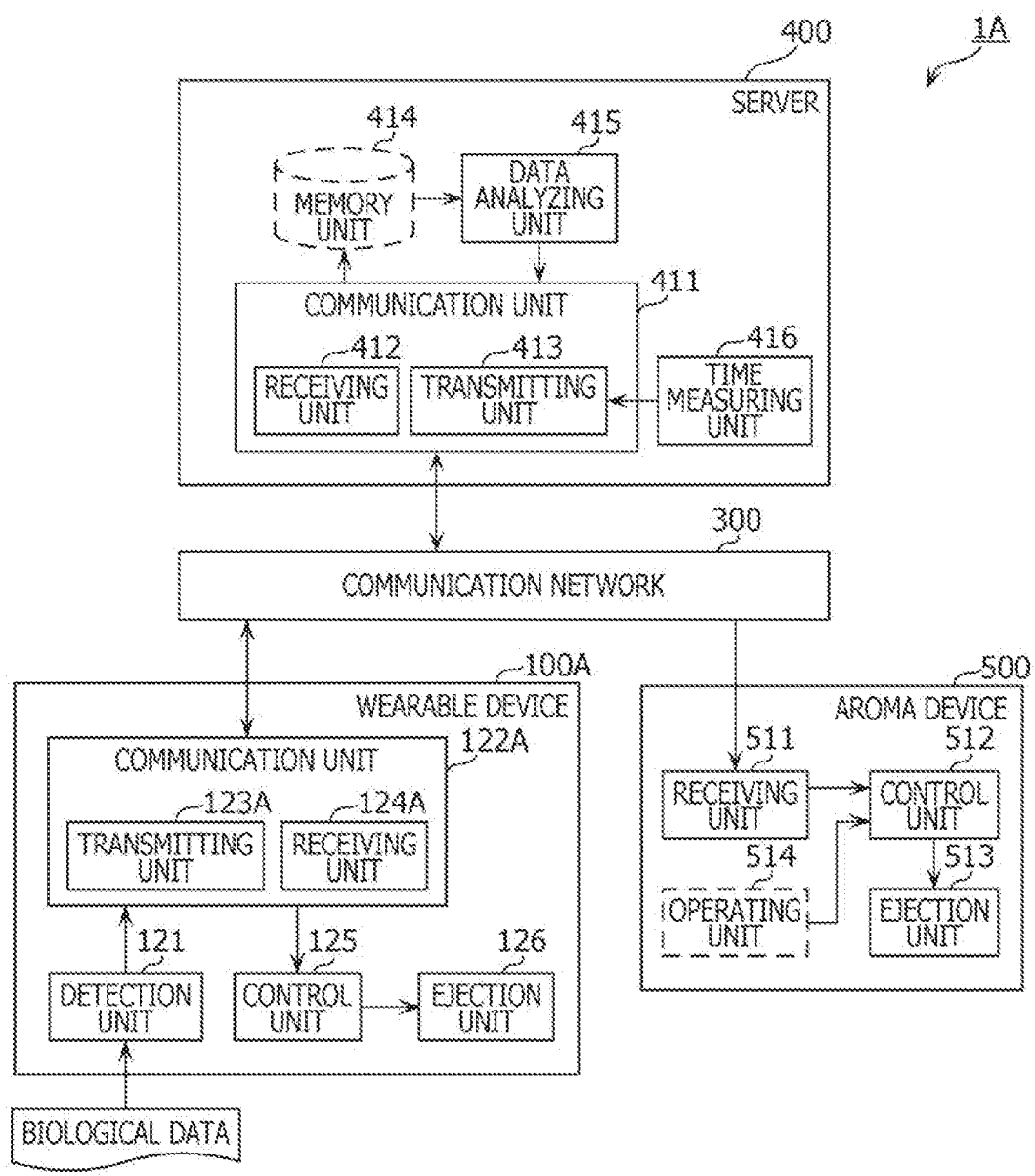
FIG. 15 is a block diagram illustrating an example of functional elements of a device control system according to Modification 1.

In the device control system 1 according to the embodiment, communication between the wearable device 100 and the server 400 is relayed by the communication terminal 200. However, the present invention is not limited to this. Specifically, it is possible to employ a device control system 1A in which a wearable device 100A and a server 400 communicate with each other without a communication terminal 200 as illustrated in FIG. 15. FIG. 15 is a block diagram illustrating an example of functional elements of the device control system according to Modification 1.

In this case, the configuration of a communication unit 122A (a transmitting unit 123A and a receiving unit 124A) of the wearable device 100A is similar, for example, to that of the second communication unit 212 of the communication terminal 200 of the embodiment. That is, the wearable device 100A has a function of directly connecting to the communication network 300 among the communication functions of the communication terminal 200. Accordingly, the wearable device 100A is communicably connected to the communication network 300 through communication connection with a router 600 or communication connection with a base station 310 of a mobile communication system.

It also can be said that the wearable device 100A is a communication terminal 200 including a detection unit 121, a control unit 125, and an ejection unit 126. That is, the wearable device 100A may be configured as a smartphone, a tablet terminal, or the like into which a biological sensor and a device are incorporated.

Details of the configurations of the communication network 300, a server 400, and an aroma device 500 of the device control system 1A according to Modification 1 are similar to those of the communication network 300, the server 400, and the aroma device 500 of the device control system 1 of the embodiment, and therefore description thereof is omitted.

1-5-2. Modification 2

Figure 16:
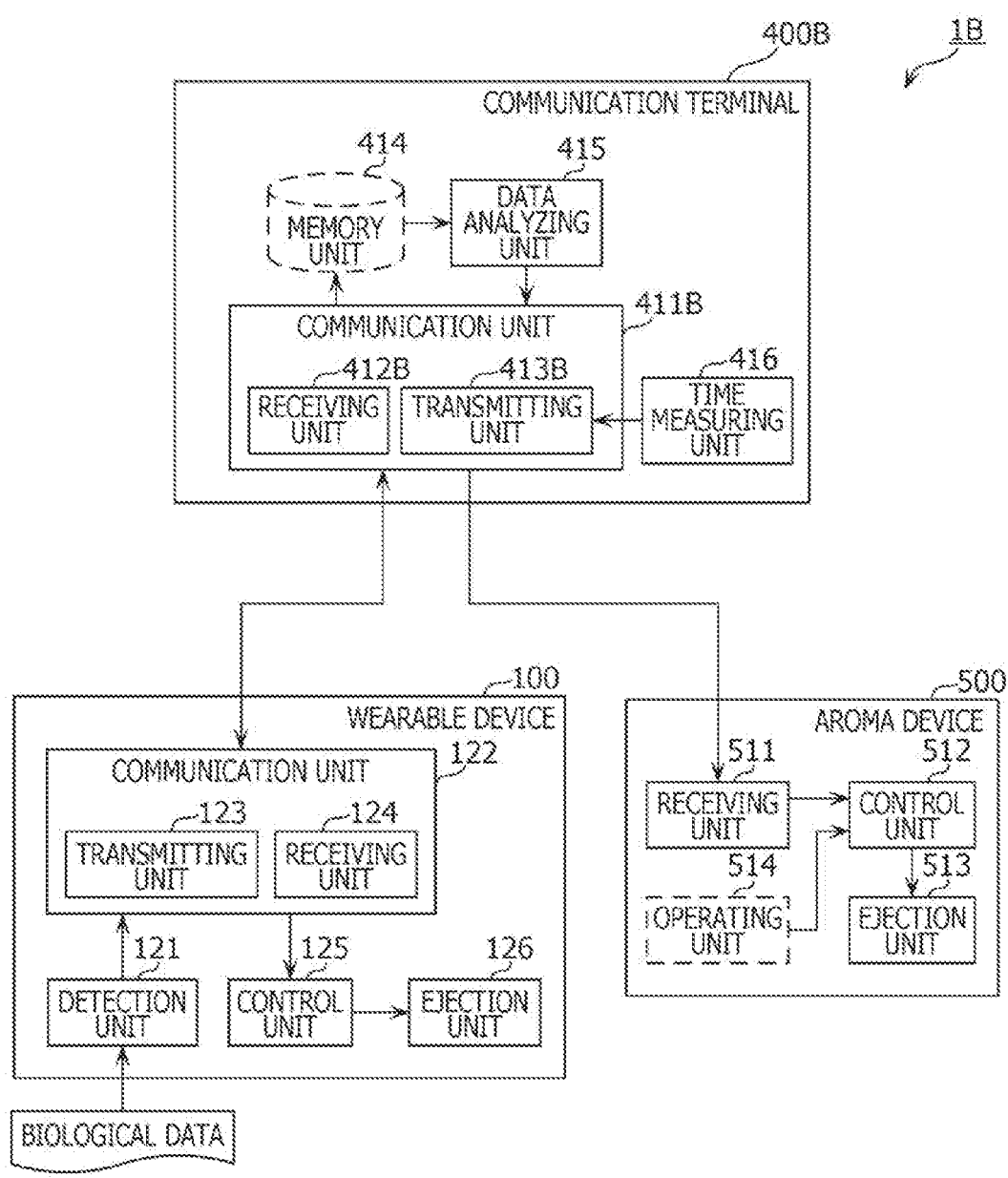
FIG. 16 is a block diagram illustrating an example of functional elements of a device control system according to Modification 2.

In the device control system 1 according to the embodiment, the server 400 connected over the communication network 300 controls the wearable device 100 and the aroma device 500 to eject a fragrance material. However, the present invention is not limited to this. Specifically, it is possible to employ a device control system 1B in which a communication terminal 400B that has the functional elements of the server 400 controls a wearable device 100 and an aroma device 500 to eject a fragrance material instead of the server 400 as illustrated in FIG. 16. FIG. 16 is a block diagram illustrating an example of functional elements of the device control system according to Modification 2.

In this case, the configuration of a communication unit 411B (a receiving unit 412B and a transmitting unit 413B) of the communication terminal 400B is similar, for example, to that of the first communication unit 211 of the communication terminal 200. That is, the communication terminal 400B may be connected to the wearable device 100 and the aroma device 500 by using Bluetooth (Registered Trademark) or may be connected to the wearable device 100 and the aroma device 500 by using wireless LAN (e.g., Wi-Fi). In the case of Wi-Fi, the communication terminal 400B is connected to the wearable device 100 and the aroma device 500 by M2M. To the aroma device 500, the communication terminal 400B may be connected by using wireless LAN via a router 600.

A memory unit 414 and a data analyzing unit 415 of the communication terminal 400B are similar to those of the server 400, and therefore detailed description thereof is omitted. The communication terminal 400B may have the functions of the position detection unit 213 and the input IF 214 of the communication terminal 200.

That is, the communication terminal 400B has a function of estimating emotion. The wearable device may have a function of estimating emotion (not illustrated).

1-5-3. Modification 3

In the device control system 1 according to the embodiment, the environment control device is the stationary-type aroma device 500 different from the wearable device 100. However, the environment control device may be a mobile device or may be the wearable device 100. That is, the server 400 may transmit a second control signal to the wearable device 100, and the wearable device 100 may eject a fragrance material at a timing at which the second control signal is received.

1-5-4. Modification 4

In the embodiment, the predetermined timing is a timing at which a user is at home. However, the present invention is not limited to this. For example, the predetermined timing may be any timing at which the user is relaxed. For example, the timing at which the user is relaxed may be a timing at which the user is taking a bath or may be a timing at which the user is lying on a sofa in a living room or on a bed in a bed room. Since a room which the user is in can be detected by detecting an ON state of lighting of a room such as a bath room, a living room, or a bed room, it can be estimated that the aforementioned timing is a timing at which the user is relaxed. In this case, information concerning ON/OFF of a lighting device of each room is transmitted to the server 400 over the communication network 300.

A room which the user is in may be detected by detecting an operation for turning on or off another electric device placed in a room instead of a lighting device. Alternatively, a room which the user is in may be detected by referring to a result obtained by a human detection sensor such as an infrared sensor placed in each room. Alternatively, use of a sofa or a bed may be detected by mounting a human detection sensor on a sofa or a bed. Alternatively, the user may hold the wearable device 100 or the communication terminal 200 over a tag placed in each room so that the wearable device 100 or the communication terminal 200 detects a room which the user is in.

In a case where the communication terminal 200 is in communication with the router 600, a room which the user is in may be detected by referring to the received signal intensity between the communication terminal 200 and the router 600. In this case, rooms and received signal intensities between the communication terminal 200 and the router 600 are associated with each other in advance.

Whether or not the user is lying on a sofa or a bed may be detected by using a result of detection by an acceleration sensor, a gyrosensor, or the like provided in the communication terminal 200.

Whether or not the user is relaxed may be determined on the basis of biological data detected by the wearable device 100.

1-5-5. Modification 5

In the server 400, the first estimation unit 421 may further estimate a degree of emotion, and a degree of positive emotion may be stored in the memory unit 414 in a case where the determining unit 422 determines that a user has positive emotion.

The determining unit 422 may determine whether or not a degree of user's positive emotion is equal to or higher than a predetermined threshold value instead of Step S135 in which the determining unit 422 determines whether or not the user has positive emotion.

1-5-6. Modification 6

In a case where it is determined two times or more within a predetermined period (e.g., 1 day) that a user has positive emotion, the server 400 may generate, upon the second detection of user's positive emotion, a first control signal for causing the wearable device 100 to eject a fragrance material containing a scent component different from that ejected upon the first detection of user's positive emotion. Similarly, the server 400 may generate, upon the third detection of user's positive emotion, a first control signal for causing the wearable device 100 to eject a fragrance material containing a scent component different from those ejected upon the first and second detection of user's positive emotion. This makes it possible to eject fragrance materials containing scent components that are different for respective user's experiences involving positive emotion.

In a case where a degree of positive emotion is stored in the memory unit 414 as in Modification 5, the server 400 may cause the kind of ejected fragrance material and a degree of positive emotion to be stored in the memory unit 414 in association with each other when transmitting a first control signal. For example, in a case where the server 400 transmits a second control signal to the aroma device 500, information indicative of the kind of fragrance material ejected in an experience involving strong positive emotion among fragrance materials ejected in user's plural experiences involving positive emotion can be included in the second control signal. Therefore, for example, the server 400 can cause the aroma device 500 to preferentially eject the kind of fragrance material ejected in the experience involving strong positive emotion. This allows the user to preferentially recall the experience involving strong positive emotion among the experiences involving positive emotion during 1 day, thereby effectively improving a user' feeling of happiness and reducing user's stress.

That is, in the wearable device 100, the device 104 ejects a fragrance material containing a scent component different from a previously ejected fragrance material by using at least one of the first fragrance material stored in the first storage unit 103a and the second fragrance material stored in the second storage unit.

1-5-7. Modification 7

In the device control system 1 according to the embodiment, a fragrance material is ejected from the wearable device 100 in a case where the server 400 determines that a user has positive emotion as a result of arithmetic processing of biological data detected by the wearable device 100, and thus an experience involving positive emotion and scent included in the fragrance material are associated with each other. However, the present invention is not limited to this. That is, a fragrance material need not be ejected from the wearable device 100 in a case where the server 400 determines that a user has positive emotion. Specifically, it is possible to employ an arrangement in which scent that is estimated to be smelled by a user is obtained by detecting scent around the user who is feeling positive emotion, and thereby correspondence between a user's experience involving positive emotion and scent is specified. In this case, a scent sensor for detecting scent need be provided in the wearable device 100.

For example, in a case where a user is feeling positive emotion while eating grilled beef, scent of grilled beef is detected, and correspondence of the scent of grilled beef and a degree of positive emotion (see Modification 5) is stored. The server 400 may cause the aroma device 500 to eject a fragrance material containing the scent of grilled beef at a predetermined timing by transmitting a second control signal including information indicative of the scent of grilled beef as a kind of scent to the aroma device 500. The scent is not limited to the scent of grilled beef and can be, for example, scent of flowers or scent of fruits that makes a user have positive emotion. For example, in a case where relatively strong scent is detected, the kind of scent has changed, or the strength of scent has changed to be stronger, correspondence between the detected scent and a degree of positive emotion may be stored upon detection of user's positive emotion instead of ejecting a fragrance material from the wearable device 100.

1-5-8. Modification 8

In the device control system 1 according to the embodiment, the second estimation unit 423 of the server 400 estimates whether or not a situation around a user is a situation where another person is close to the user, Alternatively, the second estimation unit 423 may estimate whether or not a plurality of persons are present in a space which the user is in. In this case, the deciding unit 424 may decide to use a fragrance material containing a scent component which all of the plurality of persons including the user like. In this case, it is necessary to acquire information for identifying the plurality of persons present in the same space and to acquire information indicative of a favorite scent component of the plurality of persons. For example, in a case where the plurality of persons own the wearable device 100, the user identification information may be acquired from the wearable device 100. The information indicative of the favorite scent component of the plurality of persons may be, for example, generated on the basis of input by the plurality of persons at the start of use of the wearable device 100.

1-5-9. Modification 9

The wearable device 100 according to the embodiment includes the biological sensor 101 that detects biological data of a user. However, the wearable device 100 may be configured not to include the biological sensor 101. That is, the wearable device 100 may be configured to acquire biological data of a user from an external biological sensor for detecting biological data of the user.

1-5-10. Modification 10

The communication terminal 200 according to the embodiment includes the GPS module 204. However, the communication terminal 200 may be configured not to include the GPS module 204. That is, the communication terminal may be configured to acquire positional information indicative of an estimated position from another external device including a GPS module that estimates the position of a user.

1-6. Other Remarks

In the embodiment, the constituent elements may be realized by dedicated hardware or may be realized by execution of software programs appropriate for the respective constituent elements. The constituent elements may be realized in a manner such that a program execution unit such as a CPU or a processor reads out and executes software programs recorded on a recording medium such as a hard disc or a semiconductor memory. Software for realizing the fragrance material ejection method in the embodiment is the following program.

Specifically, this program causes a first computer of a wearable device to execute a fragrance material ejection method performed by the wearable device including a biological sensor that detects biological data of a user, a first communication interface that communicates with an information processing device, a storage unit in which a fragrance material containing a predetermined scent component is stored, a device that ejects the fragrance material stored in the storage unit, and the first computer, the fragrance material ejection method including detecting, by the biological sensor, the biological data of the user; transmitting, by the first computer, the biological data detected by the biological sensor to the information processing device by using the first communication interface; receiving, by the first computer, a first control signal from the information processing device by using the first communication interface; and ejecting, by the first computer, the fragrance material stored in the storage unit of the wearable device by using the device of the wearable device at a timing at which the first control signal is received.

Software for realizing the device control method in the embodiment is the following program.

Specifically, this program causes a computer of an information processing device to execute a device control method performed by the computer of the information processing device that is communicably connected to a wearable device and an environment control device, the device control method including receiving biological data of a user detected by a biological sensor provided in the wearable device; estimating user's emotion by arithmetic processing of the received biological data; determining whether or not the estimated user's emotion is positive emotion; ejecting a fragrance material from a device for ejecting the fragrance material that is provided in the wearable device in a case where it is determined that the user's emotion is positive emotion; determining whether or not a predetermined timing has arrived after ejection of the fragrance material; and ejecting the fragrance material from the environment control device holding the fragrance material in a case where the predetermined timing has arrived.

In the present disclosure, all or a part of any of unit or device or all or a part of functional blocks in the block diagrams illustrated in FIGS. 6, 7, 15, and 16 may be implemented as one or more electronic circuits including a semiconductor device, a semiconductor integrated circuit (IC) or a large scale integration (LSI). The LSI or IC can be integrated into one chip, or also can be a combination of plural chips. For example, functional blocks other than a memory may be integrated into one chip. The name used here is LSI or IC, but it may also be called system LSI, very large scale integration (VLSI), or ultra large scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can be used for the same purpose.

Furthermore, it is also possible that all or a part of the functions or operations of the unit, device, or part of the device are implemented by executing software. In such a case, the software is recorded on one or more non-transitory recording media such as a ROM, an optical disk, or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

A device control system, a wearable device, an information processing device, a fragrance material ejection method, and a device control method according to one or more aspects of the present disclosure have been described above on the basis of the embodiment. However, the present disclosure is not limited to this embodiment. Various modifications of the present embodiment which a person skilled in the art can think of and combinations of constituent elements in different embodiments may also be encompassed within the scope of the one or more aspects of the present disclosure without departing from the spirit of the present disclosure.

The present disclosure is useful as a device control system, a wearable device, an information processing device, a fragrance material ejection method, a device control method, and the like that make it possible to improve a user's feeling of happiness and reduce user's stress.

What is claimed is:

1. A device control system, comprising:
   a wearable device; and
   an information processing device,
   the wearable device including
      a storage in which a fragrance material containing a predetermined scent component is stored,
      a device that ejects the fragrance material stored in the storage,
      a biological sensor that detects biological data of a user,
      a first communication interface, and
      a first computer,
      the first computer transmitting the biological data detected by the biological sensor by using the first communication interface, receiving a first control signal for causing the wearable device to eject the fragrance material by using the first communication interface, and causing the device to eject the fragrance material upon receipt of the first control signal,
   the information processing device including
      a second communication interface, and
      a second computer,
      the second computer receiving the biological data detected by the wearable device by using the second communication interface, estimating user's emotion by arithmetic processing of the received biological data, determining whether or not the user has positive emotion by using a result of the estimation, and in a case where it is determined that the user has positive emotion, (i) transmitting the first control signal to the wearable device by using the second communication interface, and (ii) transmitting, to an environment control device holding the fragrance material, a second control signal for causing the environment control device to eject the fragrance material at a predetermined timing after the transmission of the first control signal by using the second communication interface.

2. The device control system according to claim 1, wherein the second computer further receives positional information indicative of a current position of the user by using the second communication interface and transmits the second control signal to the environment control device at a timing at which it is determined that the current position indicated by the positional information is included in a predetermined positional range as the predetermined timing.

3. The device control system according to claim 1, wherein the second computer further counts a current time and transmits the second control signal to the environment control device at a timing at which the counted current time reaches a predetermined time as the predetermined timing.

4. The device control system according to claim 1, wherein the second computer further receives positional information indicative of a current position of the user and schedule information indicative of schedule of the user by using the second communication interface, estimates a situation around the user on basis of a current time, the positional information, and the schedule information, decides at least one of kind and amount of fragrance material to be ejected from the wearable device in accordance with the estimated situation around the user, and transmits, as the first control signal to the wearable device, a control signal for causing the wearable device to eject a fragrance material specified by the at least one of the kind and amount; and
the first computer causes the device to eject the fragrance material specified by the at least one of the kind and amount in accordance with the received first control signal.

5. The device control system according to claim 4, wherein the second computer estimates whether or not the situation around the user is a situation where another person is present within a predetermined distance from the user and makes the amount smaller in a case where it is estimated that another person is present within the predetermined distance from the user than in a case where it is estimated that no other person is present within the predetermined distance from the user.

6. The device control system according to claim 4, wherein the second computer estimates whether or not the situation around the user is a situation where the user is in middle of eating and decides to use scent of forests as the kind in a case where it is estimated that the user is in middle of eating and decides to use any kind of scent as the kind in a case where it is estimated that the user is not in middle of eating.

7. The device control system according to claim 1, wherein the storage includes a first storage in which a first fragrance material containing a first scent component is stored as the fragrance material and a second storage in which a second fragrance material containing a second scent component different from the first scent component is stored as the fragrance material; and
the device ejects scent different from previously ejected scent by using at least one of the first fragrance material stored in the first storage and the second fragrance material stored in the second storage.

8. A device control system, comprising:
   a wearable device; and
   an information processing device,
   the wearable device including
      a plurality of storages in which fragrance material containing a plurality of different predetermined scents are stored, a device that selectively ejects the fragrance material containing the plurality of different predetermined scents stored in the plurality of storages,
a biological sensor that detects biological data of a user,
a first communication interface, and
a first computer,
the first computer transmitting the biological data detected by the biological sensor by using the first communication interface, receiving a first control signal for causing the wearable device to selectively eject the fragrance material containing the plurality of different predetermined scents by using the first communication interface, and causing the device to selectively eject the fragrance material containing the plurality of different predetermined scents upon receipt of the first control signal,
the information processing device including
a second communication interface, and
a second computer,
the second computer receiving the biological data detected by the wearable device by using the second communication interface, estimating user's emotion by arithmetic processing of the received biological data, determining whether or not the user has positive emotion by using a result of the estimation, and in a case where it is determined that the user has positive emotion, transmitting the first control signal to the wearable device by using the second communication interface and generating identification information and recording the identification in a memory after the transmission of the first control signal.

9. A device control system, comprising:
a wearable device; and
an information processing device,
the wearable device including
a first communication interface, and
a first computer,
the first computer storing, in a memory, scent information indicative of a designated scent that is estimated to have been smelled by a user who is wearing the wearable device when the user has positive emotion and transmitting the scent information by using the first communication interface,
the information processing device including
a second communication interface, and
a second computer,
the second computer receiving the scent information by using the second communication interface and transmitting, to an environment control device holding a fragrance material containing the plurality of different predetermined scents, a control signal for causing the environment control device to selectively eject the fragrance material containing the designated scent indicated by the received scent information at a predetermined timing by using the second communication interface.

10. A wearable device, comprising:
a plurality of storages in which fragrance material containing a plurality of different predetermined scents are stored;
an ejector that selectively ejects the fragrance material containing the plurality of different predetermined scents stored in the plurality of storages;
a biological sensor that detects biological data of a user;
a communication interface; and
a computer,
the computer transmitting the biological data detected by the biological sensor by using the communication interface, receiving a control signal for causing the wearable device to selectively eject the fragrance material containing the plurality of different predetermined scents by using the communication interface, and controlling the ejector to selectively eject the fragrance material containing the plurality of different predetermined scents upon receipt of the control signal,
wherein a normal designated amount of fragrance material ejected is reduced to a lower designated amount by referring to a table in a memory when a person is within a predetermined distance of a user of the wearable device.

11. A wearable device according to claim 10,
wherein the ejector comprises a piezoelectric element that generates an ultrasonic wave that atomizes the fragrance material.

12. A wearable device according to claim 10,
wherein the lower designated amount is determined on the basis of a current time, positional information, and schedule information.

13. An information processing device that is communicably connected to a wearable device and an environment control device, comprising:
a communication interface; and
a computer,
the computer receiving biological data of a user wearing the wearable device by using the communication interface, the biological data being detected by the wearable device, estimating user's emotion by arithmetic processing of the received biological data, determining whether or not the user has positive emotion by using a result of the estimation, and in a case where it is determined that the user has positive emotion, (i) transmitting, to the wearable device holding a fragrance material, a first control signal for causing the wearable device to eject the fragrance material by using the communication interface, and (ii) transmitting, to the environment control device holding the fragrance material, a second control signal for causing the environment control device to eject the fragrance material at a predetermined timing after the transmission of the first control signal by using the communication interface.

14. A fragrance material ejection method performed by a wearable device including a plurality of storages that store a plurality of different predetermined scents, the fragrance material ejection method comprising:
detecting, by a biological sensor of the wearable device, the biological data of the user;
transmitting, by a computer of the wearable device, the biological data detected by the biological sensor to an information processing device by using a communication interface of the wearable device;
receiving, by the computer, a control signal from the information processing device by using the communication interface; and
controlling, by the computer, an ejector of the wearable device to selectively eject the fragrance material containing the plurality of different predetermined scents stored in the plurality of storages of the wearable device upon receipt of the control signal,
wherein a normal designated amount of fragrance material ejected is reduced to a lower designated amount by referring to a table in a memory when a person is within a predetermined distance of a user of the wearable device.

15. A fragrance material ejection method according to claim 14,
wherein the ejector comprises a piezoelectric element that generates an ultrasonic wave that atomizes the fragrance material.

16. A fragrance material ejection method according to claim 14,
wherein the lower designated amount is determined on the basis of a current time, positional information, and schedule information.

17. A device control method performed by a computer provided in an information processing device that is communicably connected to a wearable device and an environment control device, the device control method comprising:

receiving biological data of a user detected by a biological sensor provided in the wearable device;

estimating user's emotion by arithmetic processing of the received biological data;

determining whether or not the estimated user's emotion is positive emotion;

causing a device for ejecting a fragrance material provided in the wearable device to eject the fragrance material in a case where it is determined that the user's emotion is positive emotion;

determining whether or not a predetermined timing has arrived after the ejection of the fragrance material; and causing the environment control device holding the fragrance material to eject the fragrance material in a case where it is determined that the predetermined timing has arrived.

* * * * *